United States Patent
Nakayama

(10) Patent No.: US 9,091,917 B2
(45) Date of Patent: Jul. 28, 2015

(54) ACRYLIC ACID ESTER DERIVATIVE, POLYMER COMPOUND AND PHOTORESIST COMPOSITION

(75) Inventor: Osamu Nakayama, Niigata (JP)

(73) Assignee: KURARAY CO., LTD., Kurashiki-shi (JP)

( * ) Notice: Subject to any disclaimer, the term of this patent is extended or adjusted under 35 U.S.C. 154(b) by 5 days.

(21) Appl. No.: 13/983,222

(22) PCT Filed: Jan. 18, 2012

(86) PCT No.: PCT/JP2012/050981
§ 371 (c)(1),
(2), (4) Date: Aug. 1, 2013

(87) PCT Pub. No.: WO2012/105321
PCT Pub. Date: Aug. 9, 2012

(65) Prior Publication Data
US 2013/0316286 A1    Nov. 28, 2013

(30) Foreign Application Priority Data
Feb. 3, 2011    (JP) .................................. 2011-021911

(51) Int. Cl.
| | | |
|---|---|---|
| G03F 7/004 | (2006.01) | |
| C07C 271/34 | (2006.01) | |
| C07D 307/14 | (2006.01) | |

(Continued)

(52) U.S. Cl.
CPC ............ *G03F 7/0397* (2013.01); *C07C 271/34* (2013.01); *C07D 307/20* (2013.01); *C07D 309/10* (2013.01); *C08F 20/36* (2013.01); *C08F 220/36* (2013.01); *C07C 2101/04* (2013.01); *C07C 2101/08* (2013.01); *C07C 2101/14* (2013.01); *C07C 2103/74* (2013.01); *C08F 224/00* (2013.01); *C08F 228/06* (2013.01); *C08F 2220/365* (2013.01)

(58) Field of Classification Search
CPC ...... G03F 7/0397; C08F 24/00; C08F 224/00; C08F 232/08; C08F 220/36; C08F 2200/365; C08F 228/06; C07D 309/12; C07D 307/14; C07D 307/20; C07D 309/10; C07C 2103/74; C07C 271/34; C07C 2101/04; C07C 2101/08; C07C 2101/14
USPC ............... 430/270.1, 910; 526/270, 281, 282, 526/287, 301; 549/416, 419, 420, 421, 426, 549/478, 492, 496, 499; 560/115, 128, 157, 560/183, 185, 188, 205, 220; 43/270.1, 910
See application file for complete search history.

(56) References Cited

U.S. PATENT DOCUMENTS

| | | | |
|---|---|---|---|
| 2007/0111136 A1 | 5/2007 | Miyasaka et al. | |
| 2010/0151388 A1 | 6/2010 | Yang et al. | |
| 2013/0164675 A1* | 6/2013 | Nakayama et al. | ........ 430/270.1 |

FOREIGN PATENT DOCUMENTS

| | | |
|---|---|---|
| JP | 2001 166476 | 6/2001 |
| JP | 2001 215689 | 8/2001 |
| JP | 2011 232632 | 11/2001 |
| JP | 2003 241385 | 8/2003 |

(Continued)

OTHER PUBLICATIONS

International Search Report Issued Feb. 14, 2012 in PCT/JP12/50981 Filed Jan. 18, 2012.

*Primary Examiner* — John Chu
(74) *Attorney, Agent, or Firm* — Oblon, McClelland, Maier & Neustadt, L.L.P.

(57) ABSTRACT

Provided is a photoresist composition containing a polymer that contains, as a constituent unit, a specific methacrylic acid ester derivative. The photoresist composition can form a photoresist pattern with improved LWR and high resolution. More specifically, provided is an acrylic acid ester derivative represented by the following general formula (1):

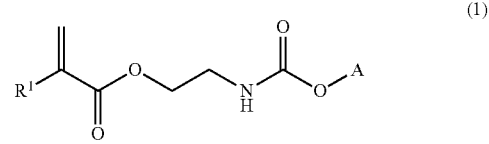

(1)

wherein $R^1$ is a hydrogen atom or a methyl group; and A represents the following general formula (A-1) or (A-2):

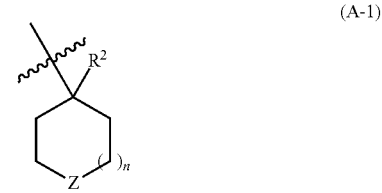

(A-1)

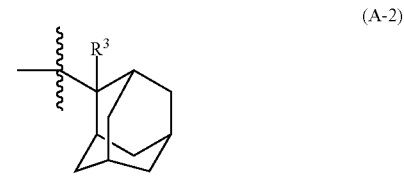

(A-2)

wherein $R^2$ and $R^3$ are each independently an alkyl group having 1 to 6 carbon atoms or a cyclic hydrocarbon group having 3 to 6 carbon atoms; Z is $CH_2$ or —O—; and n is 0 or 1; with the proviso that in (A-1) there is no case where $R^2$ is a methyl group and Z is $CH_2$ and n is 1.

19 Claims, No Drawings

(51) Int. Cl.
*C07D 309/12* (2006.01)
*C08F 220/36* (2006.01)
*C08F 224/00* (2006.01)
*C08F 228/06* (2006.01)
*G03F 7/039* (2006.01)
*C07D 307/20* (2006.01)
*C07D 309/10* (2006.01)
*C08F 20/36* (2006.01)

(56) References Cited

FOREIGN PATENT DOCUMENTS

| | | |
|---|---|---|
| JP | 2007 106929 | 4/2007 |
| JP | 2009 063610 | 3/2009 |
| JP | 2010 224558 | 10/2010 |
| JP | 2011 209667 | 10/2011 |
| JP | 2011232632 A | * 11/2011 |

* cited by examiner

ACRYLIC ACID ESTER DERIVATIVE, POLYMER COMPOUND AND PHOTORESIST COMPOSITION

This application is a 371 of PCT/JP2012/050981, filed Jan. 18, 2012. Priority to Japanese patent application 2011-021911, filed Feb. 3, 2011, is claimed.

TECHNICAL FIELD

The present invention relates to an acrylic acid ester derivative, a polymer containing a structural unit derived from the acrylic acid ester derivative, and a photoresist composition which can form a photoresist pattern with improved line width roughness (LWR) and high resolution.

BACKGROUND ART

A lithography technique comprises, for example, steps of forming a photoresist film comprising a photoresist material on a substrate, selectively exposing the photoresist film to radiation such as light, electron beam, and the like through a mask having a predetermined pattern formed thereon, and performing a development treatment to form a photoresist pattern of predetermined shape on the photoresist film. In addition, the photoresist material is referred to as a positive tone photoresist material when the portion thereof exposed to the radiation becomes soluble in a developer. And, the photoresist material is referred to as a negative tone photoresist material when the portion thereof exposed to the radiation becomes insoluble in the developer.

Recently, in the production of semiconductor devices and liquid crystal display devices, the pattern is rapidly becoming finer due to the progress in lithographic technology. As a method for fine patterning, generally, the use of a shorter-wavelength (higher-energy) exposure light source is practiced. Heretofore, ultraviolet light represented by g-line and i-line has been used but, at present, quantity production of semiconductor devices by the use of a KrF excimer laser and an ArF excimer laser has started. Further, also under study is lithography using an $F_2$ excimer laser, an electron beam, EUV (extreme ultraviolet light), an X-ray, and the like having shorter wavelength (higher energy) than the KrF excimer laser and the ArF excimer laser.

The photoresist materials are required to have lithography characteristics such as sensitivity to these exposure light sources, resolution capability to reproduce a fine dimension pattern, and the like. As a photoresist material which satisfies these requirements, there is used a chemically amplified photoresist composition comprising a base material component which changes its solubility in an alkaline developer by the action of an acid and an acid generator component which generates an acid upon exposure.

For example, as a chemically amplified positive tone photoresist composition, there is generally used a photoresist composition comprising a resin component (a base resin), solubility of which in an alkaline developer increases by the action of an acid, and an acid generator component. When a photoresist film formed using the photoresist composition is selectively exposed to light during photoresist patterning, an acid is generated from the acid generator component in the exposed portion and, by the action of the acid, solubility of the resin in the alkaline developer increases, and the exposed portion becomes soluble in the alkaline developer.

Currently, as a base resin of a photoresist material for use in ArF excimer laser lithography and the like, the so-called acrylic resin which has a structural unit derived from a (meth) acrylic acid ester in the main chain is generally used as a polymer which is a component of the photoresist composition, because the acrylic resin has excellent transparency in the vicinity of 193 nm (see, for example, Patent Literature 1).

In addition, it is also under study to blend a nitrogen-containing organic compound such as an alkyl amine, an alkyl alcohol amine, and the like into the chemically amplified photoresist composition. The nitrogen-containing organic compound acts as a quencher to trap the acid generated from the acid generator and contributes to improvement of the lithography characteristics such as the shape of the photoresist pattern and the like. As the nitrogen-containing organic compound, a tertiary amine is generally widely used. However, as the photoresist pattern becomes finer, use of a nitrogen-containing organic compound having a carbamate group has also become known in order to improve a process margin and the like in forming an isolated pattern (see, for example, Patent Literatures 2 and 3). Furthermore, there is proposed a base resin containing, as one of the repeating units, a (meth) acrylic acid ester having a carbamate group (see, for example, Patent Literature 4).

CITATION LIST

Patent Literature

Patent Literature 1: Japanese Patent Laid-Open Publication No. 2003-241385
Patent Literature 2: Japanese Patent Laid-Open Publication No. 2001-166476
Patent Literature 3: Japanese Patent Laid-Open Publication No. 2001-215689
Patent Literature 4: US Patent No. 2010/0151388

SUMMARY OF INVENTION

Technical Problem

However, as described above, fine patterning is rapidly advancing in recent years in the production of semiconductor devices and liquid crystal display devices in accordance with the progress in lithographic technology. Thus, at present, there is a strong need for development of a photoresist material which can improve more than ever the various lithography characteristics such as resolution capability, line width roughness (LWR), and the like, as well as the pattern shape. Although the photoresist composition containing a nitrogen-containing organic compound having a carbamate group, described in Patent Literatures 2 and 3, and a photoresist composition containing a base resin containing as one of the repeating units a (meth)acrylic acid ester having a carbamate group, described in Patent Literature 4, show a certain degree of improvement effect, they cannot yet satisfy the lithography characteristics and pattern shape required by advances in fine patterning.

The present invention was made in view of the above-described circumstances and its objects are to provide a novel acrylic acid ester derivative which can become a structural unit of a polymer to be contained in a photoresist composition, to provide a polymer containing a structural unit derived from the acrylic acid ester derivative, and to provide a photoresist composition containing the polymer, which can form a photoresist pattern with more improved LWR and higher resolution than before.

Solution to Problem

The present inventors conducted diligent research and, as a result, have found that a photoresist composition using a polymer obtained by polymerizing raw materials containing a specific acrylic acid ester derivative can form a photoresist pattern with more improved LWR and higher resolution than before.

That is, the present invention provides the following [1] to [3].

[1] An acrylic acid ester derivative (hereinafter referred to as acrylic acid ester derivative (1)) represented by the following general formula (1):

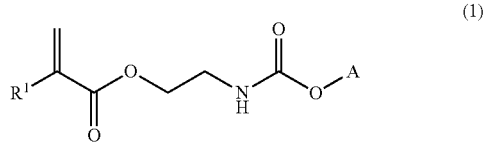

wherein $R^1$ is a hydrogen atom or a methyl group; and A represents the following general formula (A-1) or (A-2):

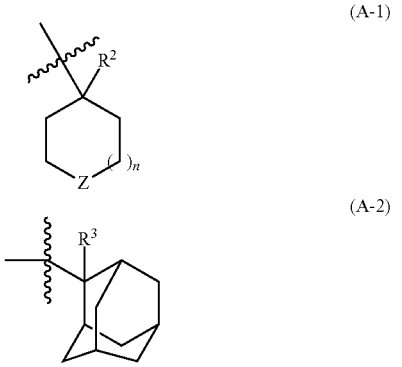

wherein $R^2$ and $R^3$ are each independently an alkyl group having 1 to 6 carbon atoms or a cyclic hydrocarbon group having 3 to 6 carbon atoms; Z is $CH_2$ or —O—; and n is 0 or 1; with the proviso that in (A-1) there is no case where $R^2$ is a methyl group and Z is $CH_2$ and n is 1.

[2] A polymer containing a structural unit derived from the acrylic acid ester derivative (1) according to [1] above.

[3] A photoresist composition comprising the polymer according to [2] above, a photoacid generator, and a solvent.

Advantageous Effects of Invention

According to the photoresist composition using the polymer obtained by polymerizing raw materials containing the acrylic acid ester derivative (1) of the present invention, a photoresist pattern with improved LWR and high resolution can be formed.

DESCRIPTION OF EMBODIMENTS

[Acryl Acid Ester Derivative (1)]

The acrylic acid ester derivative (1) is characterized in that it has, at its molecular end, a structure derived from a specific tertiary alcohol having a cyclic structure through a carbamate bond. A photoresist composition using a polymer containing a structural unit derived from the acrylic acid ester derivative (1) can form a photoresist pattern with more improved LWR and higher resolution. Although the mechanism by which the effects of the present invention are exhibited is not clear, it is presumed that the base resin containing a functional group which is dissociated by an acid forms a carboxyl group by an acid generated from the photoacid generator and its solubility in a basic developer increases; and, at the same time, when a structural unit derived from the acrylic acid ester derivative (1) of the present invention reacts with the acid generated from the photoacid generator, the alcohol portion is detached with evolution of $CO_2$ and generates an amino group, which quenches the acid before it diffuses excessively into the photoresist film.

The alkyl group having 1 to 6 carbon atoms represented each independently by $R^2$ and $R^3$ may be linear or branched and includes, for example, a methyl group, an ethyl group, an n-propyl group, an isopropyl group, an n-butyl group, an isobutyl group, a s-butyl group, an n-pentyl group, an n-hexyl group, and the like. The cyclic hydrocarbon group having 3 to 6 carbon atoms represented each independently by $R^2$ and $R^3$ includes a cyclopropyl group, a cyclobutyl group, a cyclopentyl group, and a cyclohexyl group.

Among these, from the viewpoint of improved LWR, it is preferable that $R^2$ and $R^3$ are each independently an alkyl group having 1 to 3 carbon atoms.

Specific examples of the acrylic acid ester derivative (1) are shown in the following but the present invention is not particularly limited to these. However, in the general formula (A-1), there is no case where $R^2$ is a methyl group and Z is $CH_2$ and n is 1.

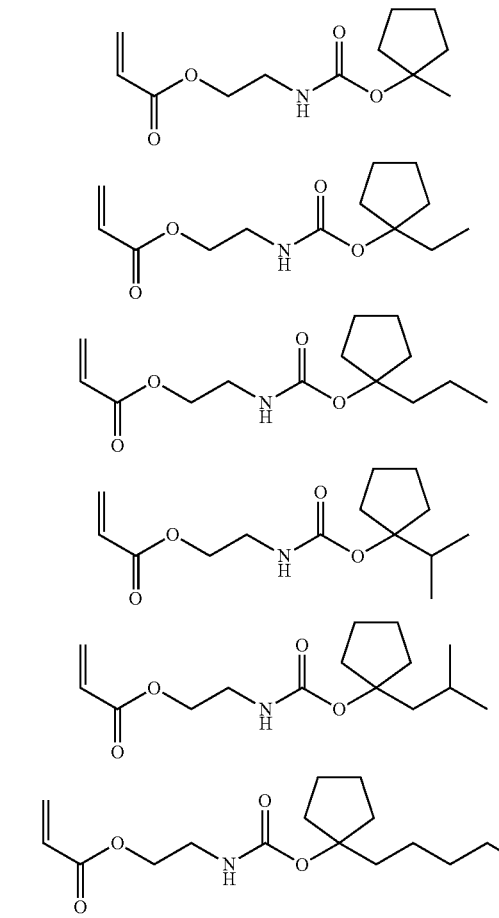

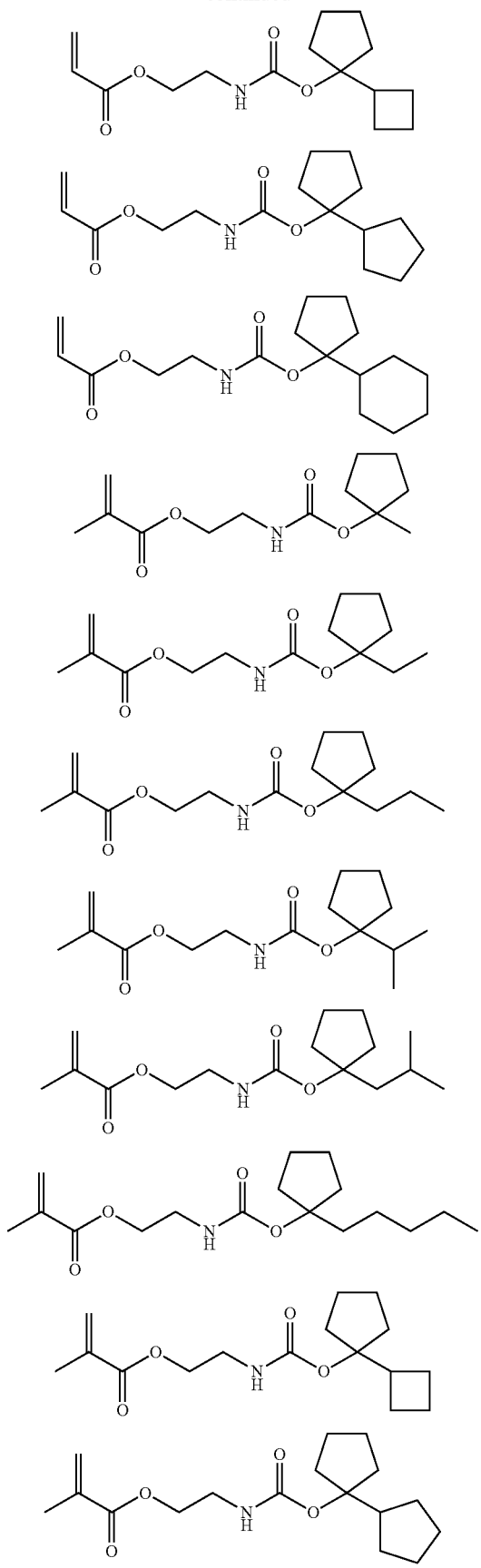
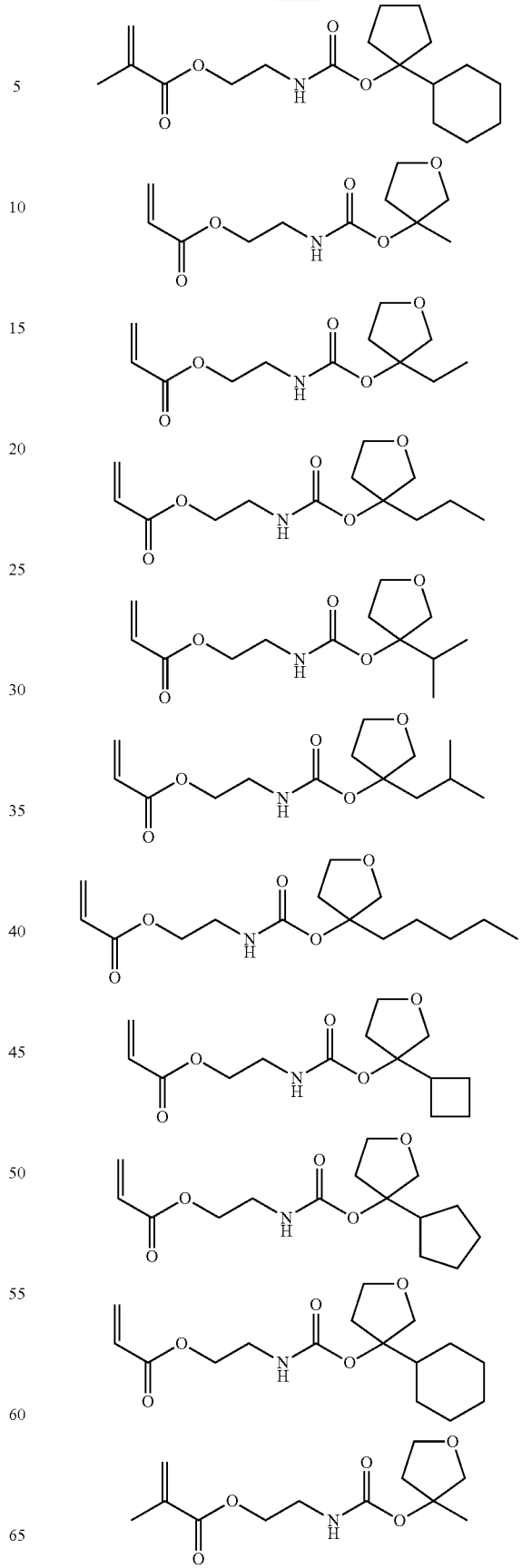

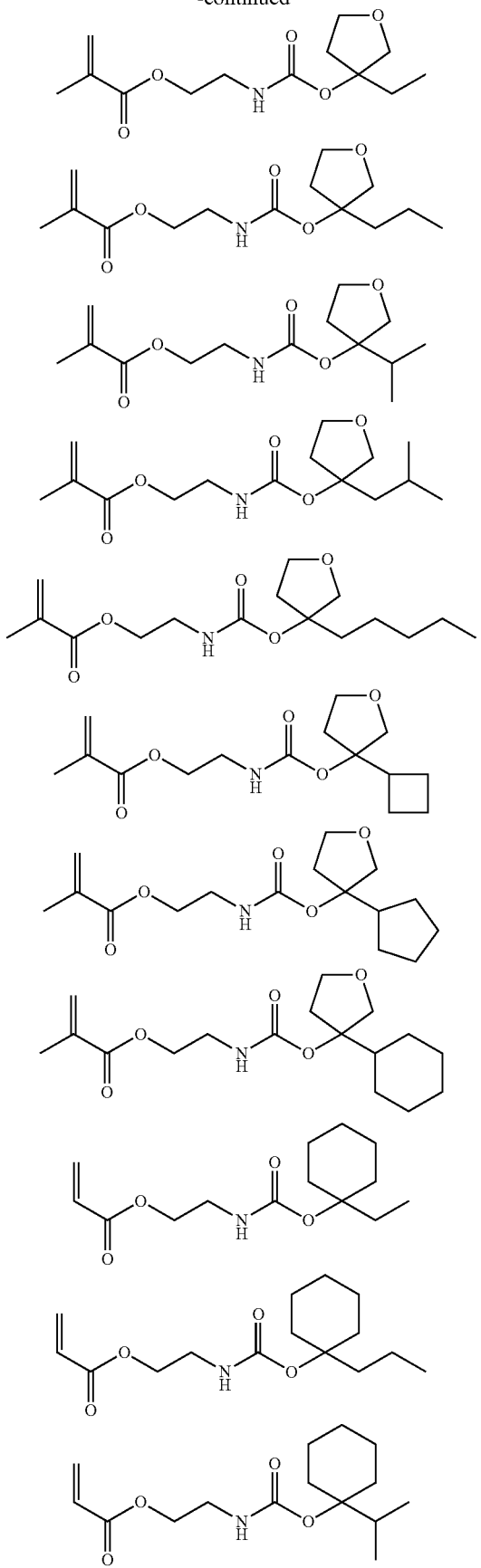
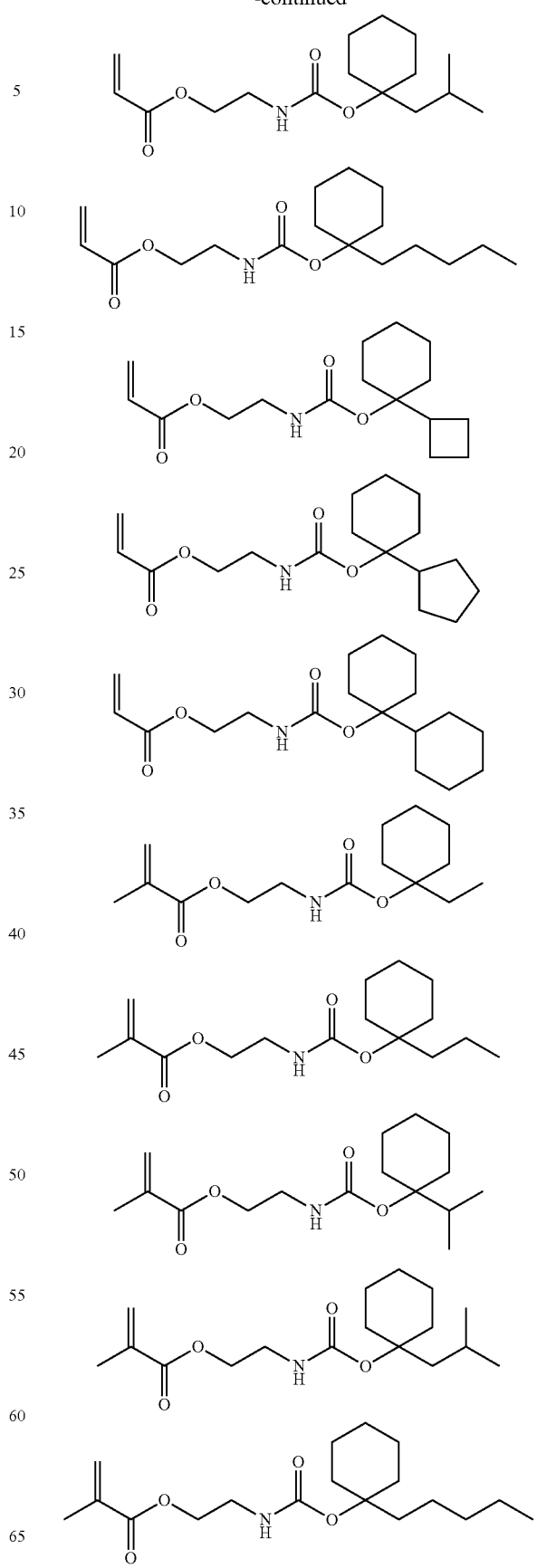

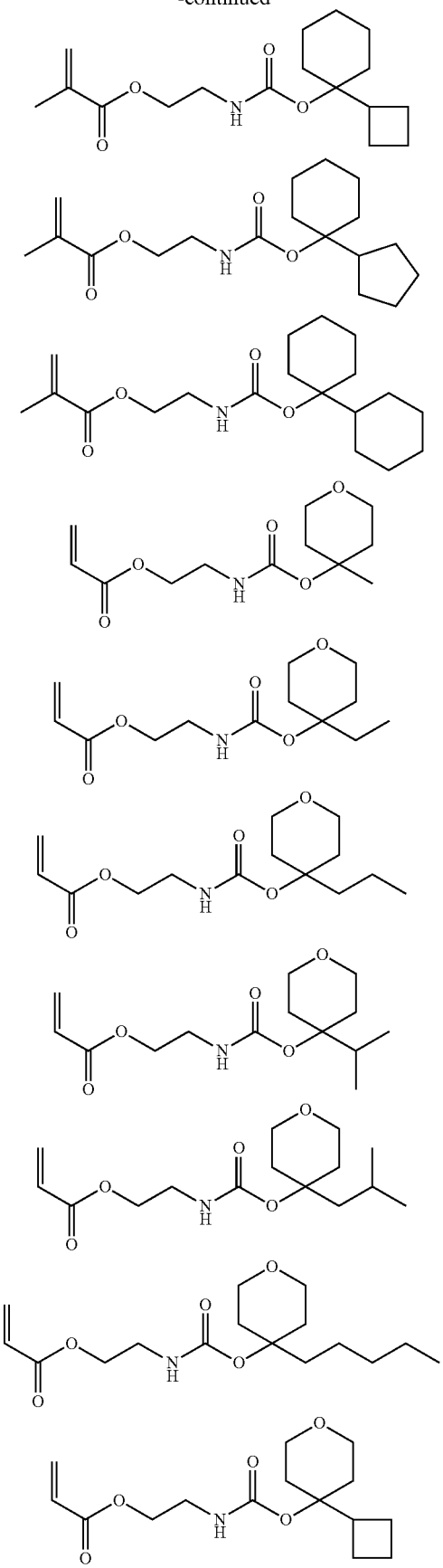
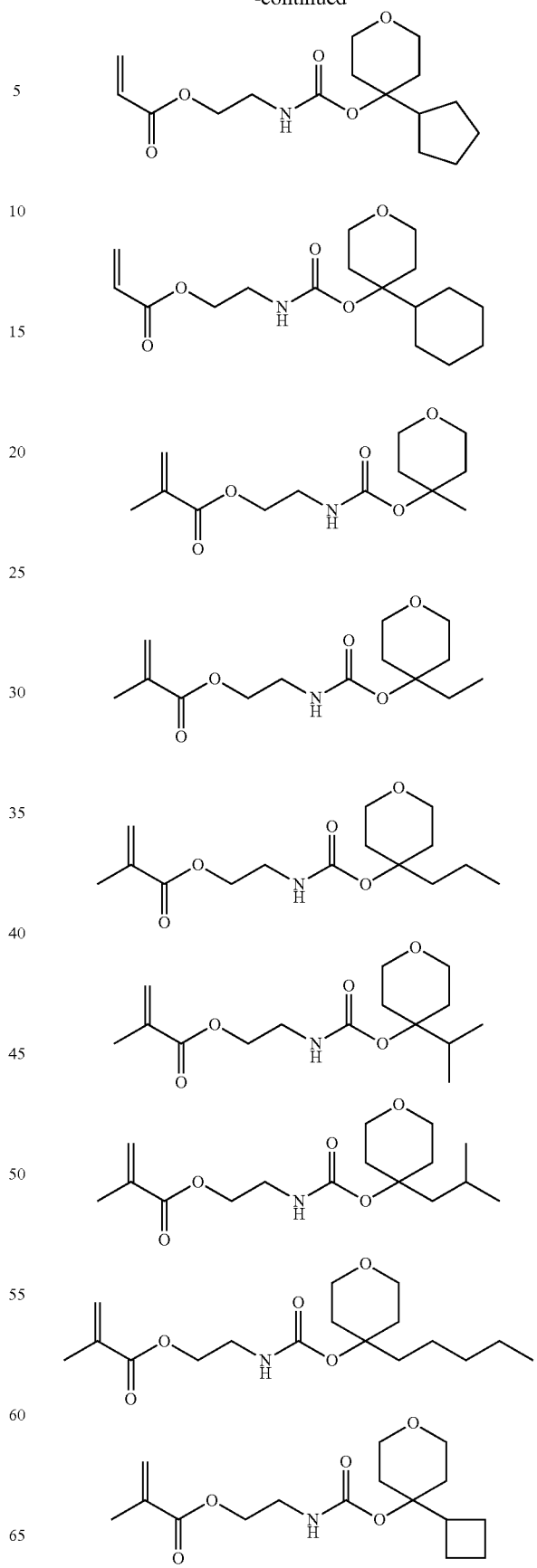

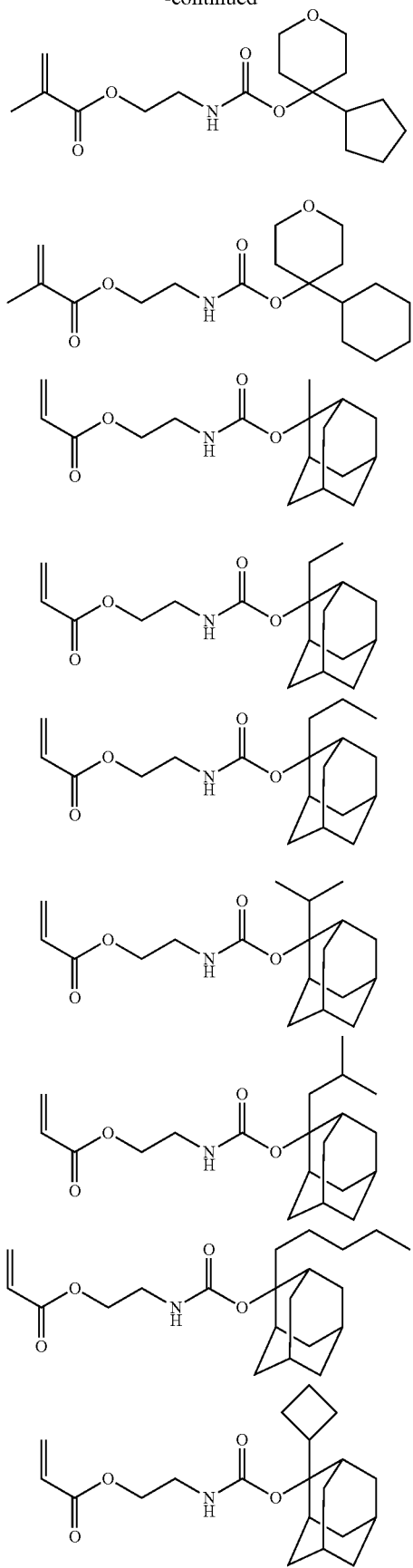
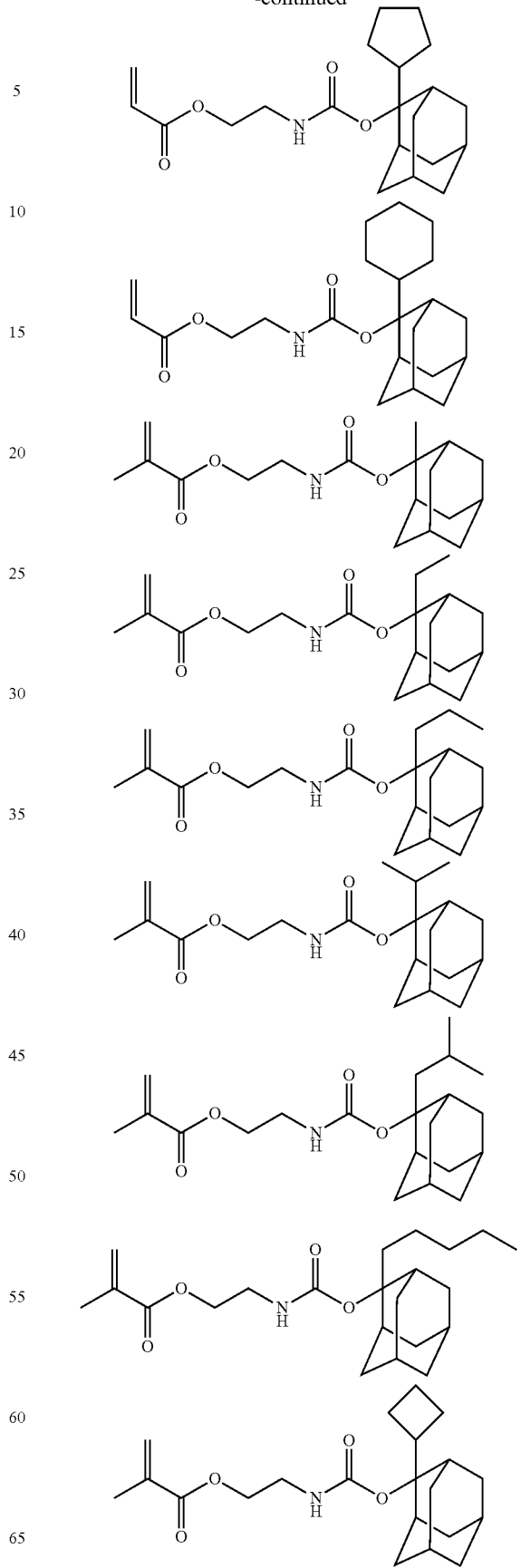

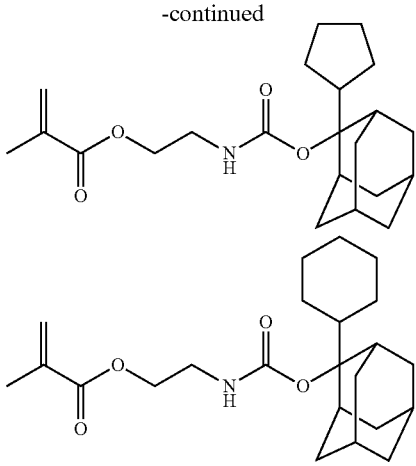

(Process for Producing the Acrylic Acid Ester Derivative (1))

The process for producing the acrylic ester derivative (1) of the present invention is not particularly limited. However, for example, as shown in the following, it can be produced by reacting an isocyanate derivative (hereinafter referred to as isocyanate derivative (2)) and an alcohol derivative (hereinafter referred to as alcohol derivative (3)) in the presence of, if necessary, a catalyst, a polymerization inhibitor, a solvent, and the like. Hereinafter, this reaction is referred to as "reaction (a)."

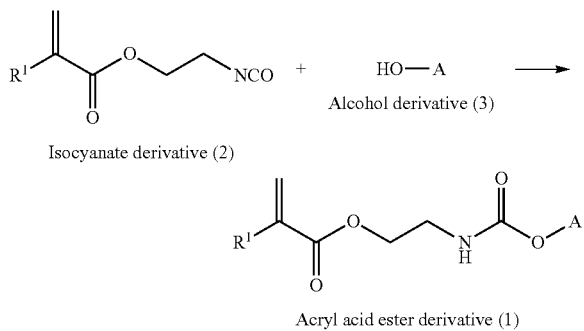

(In the formula, $R^1$ and A are as defined previously.)

Hereinafter, the reaction (a) will be described in detail.

The isocyanate derivative (2) includes 2-acryloyloxyethyl isocyanate and 2-methacryloyloxyethyl isocyanate.

The amount of the isocyanate derivative (2) used is preferably 0.8 to 5 moles per 1 mole of the alcohol derivative (3) and, from the viewpoint of economic efficiency and ease of after-treatment, more preferably 1 to 3 moles.

There is no particular limitation how the alcohol derivative (3) is obtained. Some may be obtained commercially and some may be produced by processes which have been made public through patent literatures or non-patent literatures.

The reaction (a) may be carried out in the presence or absence of a catalyst. The catalyst which can be used includes mineral acids such as hydrochloric acid, sulfuric acid, and the like; carboxylic acids such as formic acid, acetic acid, trifluoroacetic acid, and the like; sulfonic acids such as methanesulfonic acid, toluenesulfonic acid, trifluoromethanesulfonic acid, and the like; Lewis acids such as boron trifluoride, aluminum trichloride, dibutyltin dilaurate, and the like; tertiary amines such as triethylamine, tributylamine, N,N-dimethylaniline, 1,4-diazabicyclo[2.2.2]octane, 1,5-diazabicyclo[4.3.0]non-5-ene, 1,8-diazabicyclo[5.4.0]undec-7-ene, and the like: nitrogen-containing heterocyclic aromatic compounds such as pyridine, 2-methylpyridine, 4-(dimethylamino)pyridine, and the like; and the like.

From the viewpoint of the reaction rate, the reaction (a) is preferably carried out in the presence of a catalyst. Further, the catalysts may be used singly or in combination of two or more kinds unless an acid is mixed with a base.

When the reaction is carried out in the presence of a catalyst, the amount thereof used relative to 1 mole of the alcohol derivative (3) is preferably 0.001 to 0.7 mole and more preferably 0.01 to 0.5 mole.

The reaction (a) may be carried out in the presence or in the absence of a polymerization inhibitor. The polymerization inhibitor which can be used is not particularly limited and includes, for example, quinone compounds such as hydroquinone, methoxyphenol, benzoquinone, toluquinone, p-t-butylcatechol, and the like; alkylphenol compounds such as 2,6-di-t-butylphenol, 2,4-di-t-butylphenol, 2-t-butyl-4,6-dimethylphenol, and the like; amine compounds such as phenothiazine and the like; 2,2,6,6-tetramethylpiperidine-N-oxyl compounds such as 2,2,6,6-tetramethylpiperidine-N-oxyl, 4-acetamido-2,2,6,6-tetramethylpiperidine-N-oxyl, and the like; and the like. These may be used singly or in combination of two or more kinds.

When a polymerization inhibitor is used, the amount thereof used, relative to the mass of the whole reaction mixture except the after-mentioned solvent, is preferably 0.001 to 5 mass %, more preferably 0.001 to 1 mass %, and even more preferably 0.005 to 0.5 mass %.

The reaction (a) may be carried out in the presence or absence of a solvent. The solvent which can be used is not particularly limited unless it interferes with the reaction and includes, for example, saturated hydrocarbons such as hexane, heptane, octane, cyclohexane, and the like; aromatic hydrocarbons such as benzene, toluene, xylene, and the like; halogenated hydrocarbons such as methylene chloride, 1,2-dichloroethane, chloroform, chlorobenzene, fluorobenzene, and the like; ethers such as diethyl ether, diisopropyl ether, tetrahydrofuran, 1,4-dioxane, cyclopentyl methyl ether, 1,2-dimethoxyethane, and the like; esters such as methyl acetate, ethyl acetate, propyl acetate, and the like; nitriles such as acetonitrile, propionitrile, benzonitrile, and the like; amides such as N,N-dimethylformamide, N,N-dimethylacetamide, N-methylpyrrolidone, and the like; and the like. These may be used singly or in combination of two or more kinds.

When the reaction is carried out in the presence of a solvent, the amount thereof used, relative to 1 part by mass of the alcohol derivative (3), is preferably 0.5 to 100 parts by mass and more preferably 0.5 to 20 parts by mass from the viewpoint of easiness of the after-treatment.

The reaction temperature may vary depending on the kind of the isocyanate derivative (2) and the alcohol derivative (3) used, and the catalyst and the solvent used if necessary. However, it is preferably generally −30 to 100° C. and more preferably −10 to 80° C.

Furthermore, the reaction pressure is not particularly limited but it is simple and preferable to carry out the reaction under ambient pressure.

The reaction time may vary depending on the kind of the isocyanate derivatibe (2) and the alcohol derivative (3) used, and the catalyst and solvent used if necessary. However, it is preferably generally 0.5 hour to 48 hours and more preferably 1 hour to 24 hours.

From the viewpoint of safety, the reaction (a) is preferably carried out under an atmosphere of an inert gas such as nitrogen, argon, and the like.

The procedure for the reaction (a) is not particularly limited. The method and order of addition of each reagent are also not particularly limited and the reagents may be introduced by any method and order. However, preferable is a process where the alcohol derivative (3), the isocyanate derivative (2), and, if necessary, the solvent are charged in a batch reactor and, when the reaction temperature and the reaction pressure of this mixed solution have reached the desired values, the catalyst is added if necessary, a catalyst.

Isolation of the acrylic acid ester derivative (1) from the reaction mixture obtained by the above-mentioned process and purification thereof may be carried out by a method generally used to isolate and purify an organic compound.

For example, after the reaction is complete, the acrylic acid ester derivative (1) can be isolated by the addition of water to the reaction mixture, followed by extraction with an organic solvent and concentration of the organic layer obtained. Further, if necessary, the acrylic acid ester derivative (1) of high purity can be obtained by purification by recrystallization, distillation, silica gel column chromatography, and the like.

Also, if necessary, a metal content in the acrylic acid ester derivative (1) obtained may be reduced by filtration after addition of a chelating agent such as nitrilotriacetic acid, ethylenediaminetetraacetic acid, and the like; or by treatment with a metal removal filter such as "Zeta Plus (trademark)" (trade name, manufactured by Sumitomo 3M Ltd.), Protego (trade name, manufactured by Entegris Japan Co., Ltd., "Ion Clean" (trade name, manufactured by Nihon Pall, Ltd.), and the like.

[Polymer]

A polymer obtained by homopolymerizing the acrylic acid ester derivative (1) of the present invention or a copolymer obtained by copolymerizing the acrylic acid ester derivative (1) and other polymerizable compounds are useful as a polymer for a photoresist composition.

The polymer of the present invention contains a structural unit derived from the acrylic acid ester derivative (1) in an amount of more than 0 mole % to 40 mole % and, from the viewpoint of LWR and resolution, in an amount of preferably 0.1 to 30 mole %, more preferably 0.5 to 25 mole %, and even more preferably 1 to 20 mole %.

Specific examples of the other polymerizable compounds which can be copolymerized with the acrylic acid ester derivative (1) (hereinafter referred to as copolymerizable monomer) include, for example, the compounds shown by the following chemical formulas but the present invention is not particularly limited to these.

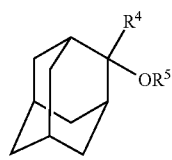
(I)

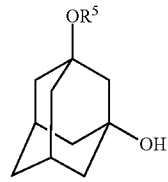
(II)

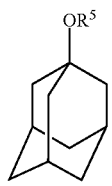
(III)

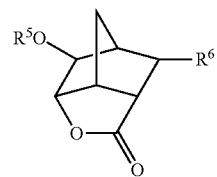
(IV)

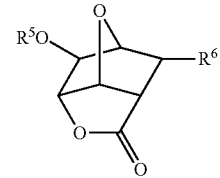
(V)

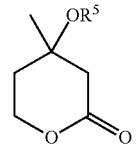
(VI)

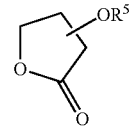
(VII)

(VIII)

(IX)

$R^5-O-R^8$
(X)

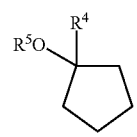
(XI)

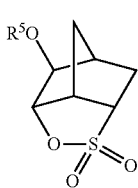
(XII)

In the above formulas (I) to (XII), $R^4$ represents a hydrogen atom or an alkyl group having 1 to 3 carbon atoms; $R^5$ represents a polymerizable group; $R^6$ represents a hydrogen atom or —COOR$^7$; $R^7$ represents an alkyl group having 1 to 3 carbon atoms; and $R^8$ represents an alkyl group having from 1 to 4 carbon atoms.

In the copolymerizable monomers, the alkyl group having 1 to 3 carbon atoms represented each independently by $R^4$ and $R^7$ includes, for example, a methyl group, an ethyl group, an n-propyl group, and an isopropyl group. The alkyl group having 1 to 4 carbon atoms represented by $R^8$ includes, for example, a methyl group, an ethyl group, an n-propyl group, an isopropyl group, an n-butyl group, an isobutyl group, a s-butyl group, a t-butyl group, and the like. Furthermore, the polymerizable group represented by $R^5$ includes, for example, an acryloyl group, a methacryloyl group, a vinyl group, a crotonoyl group, and the like.

Among the above, preferable as the copolymerizable monomer is one represented by the above formula (I), (II), (IV), (V), (VI), (VII), (XI), or (XII); and more preferable is the following combination of copolymerizable monomers:

the copolymerizable monomer represented by the formula (I), the copolymerizable monomer represented by the formula (II), and the copolymerizable monomer represented by the formula (VII);

the copolymerizable monomer represented by the formula (I), the copolymerizable monomer represented by the formula (II), and the copolymerizable monomer represented by the formula (XII);

the copolymerizable monomer represented by the formula (I), the copolymerizable monomer represented by the formula (II), the copolymerizable monomer represented by the formula (VII), and the copolymerizable monomer represented by (XII);

the copolymerizable monomer represented by the formula (XI), the copolymerizable monomer represented by the formula (II), and the copolymerizable monomer represented by the formula (VII);

the copolymerizable monomer represented by the formula (XI), the copolymerizable monomer represented by the formula (II), and the copolymerizable monomer represented by the formula (XII);

the copolymerizable monomer represented by the formula (XI), the copolymerizable monomer represented by the formula (II), the copolymerizable monomer represented by the formula (VII), and the copolymerizable monomer represented by the formula (XII);

the copolymerizable monomer represented by the formula (I), the copolymerizable monomer represented by the formula (XI), the copolymerizable monomer represented by the formula (II), and the copolymerizable monomer represented by the formula (VII);

the copolymerizable monomer represented by the formula (I), the copolymerizable monomer represented by the formula (XI), the copolymerizable monomer represented by the formula (II), and the copolymerizable monomer represented by the formula (XII); and the copolymerizable monomer represented by the formula (I), the copolymerizable monomer represented by the formula (XI), the copolymerizable monomer represented by the formula (II), the copolymerizable monomer represented by the formula (VII), and the copolymerizable monomer represented by the formula (XII).

(Process for Producing the Polymer)

The polymer can be produced by radical polymerization according to a conventional process. Especially, as a process to synthesize a polymer having a narrow molecular weight distribution, there may be mentioned living radical polymerization and the like.

In a general polymerization process, if necessary, one or more acrylic acid ester derivatives (1) and, if necessary, one or more copolymerizable monomers mentioned above are polymerized in the presence of a radical polymerization initiator, a solvent, and, if necessary, a chain transfer agent.

There is no particular limitation how the radical polymerization is carried out and there may be employed a common process used in producing an acrylic resin such as a solution polymerization process, an emulsion polymerization process, a suspension polymerization process, a bulk polymerization process, and the like.

The radical polymerization initiator includes, for example, hydroperoxide compounds such as t-butyl hydroperoxide, cumene hydroperoxide, and the like; dialkyl peroxide compounds such as di-t-butyl peroxide, t-butyl-α-cumyl peroxide, di-α-cumyl peroxide, and the like; diacyl peroxide compounds such as benzoyl peroxide, diisobutyryl peroxide, and the like; azo compounds such as 2,2'-azobisisobutyronitrile, dimethyl 2,2'-azobisisobutyrate, and the like; and the like.

The amount of the radical polymerization initiator used may be selected appropriately depending on the polymerization conditions such as the kind and amount of the acrylic acid ester derivative (1), the copolymerizable monomer, the chain transfer agent, and the solvent; polymerization temperature; and the like. However, relative to 1 mole of the total polymerizable compounds [total amount of the acrylic acid ester derivative (1) and the copolymerizable monomer; hereinafter the same shall apply], it is usually preferably 0.005 to 0.2 mole and more preferably 0.01 to 0.15 mole.

The chain transfer agent includes, for example, thiol compounds such as dodecanethiol, mercaptoethanol, mercaptopropanol, mercaptoacetic acid, mercaptopropionic acid, and the like. When the chain transfer agent is used, the amount thereof used, relative to 1 mole of the total polymerizable compounds, is usually preferably 0.005 to 0.2 mole and more preferably 0.01 to 0.15 mole.

The solvent is not particularly limited unless it interferes with the polymerization reaction and includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; esters such as ethyl lactate, methyl 3-methoxypropionate, methyl acetate, ethyl acetate, propyl acetate, and the like; ketones such as acetone, methyl ethyl ketone, methyl isopropyl ketone, methyl isobutyl ketone, methyl amyl ketone, cyclopentanone, cyclohexanone, and the like; ethers such as diethyl ether, diisopropyl ether, dibutyl ether, tetrahydrofuran, 1,4-dioxane, and the like; and the like.

The amount of the solvent used, relative to 1 part by mass of the total polymerizable compounds, is usually preferably 0.5 to 20 parts by mass and more preferably 1 to 10 parts by mass from the viewpoint of economic efficiency.

The reaction temperature is usually preferably 40 to 150° C., and more preferably 60 to 120° C. from the viewpoint of stability of the polymer formed.

The polymerization reaction time varies depending on the polymerization conditions such as the kind and amount of the acrylic acid ester derivative (1), the copolymerizable monomer, the polymerization initiator, and the solvent; polymerization reaction temperature, and the like. However, it is usually preferably 30 minutes to 48 hours and more preferably 1 hour to 24 hours.

The polymerization reaction is preferably carried out under an atmosphere of an inert gas such as nitrogen, argon, and the like.

The thus obtained polymer may be isolated by a usual operation such as reprecipitation and the like. The isolated polymer may be dried under a reduced pressure condition.

The solvent used in the reprecipitation operation includes aliphatic hydrocarbons such as pentane, hexane, and the like; alicyclic hydrocarbons such as cyclohexane and the like; aromatic hydrocarbons such as benzene, xylene, and the like; halogenated hydrocarbons such as methylene chloride, chloroform, chlorobenzene, dichlorobenzene, and the like; nitrated hydrocarbons such as nitromethane and the like; nitriles such as acetonitrile, benzonitrile, and the like; ethers such as diethyl ether, diisopropyl ether, tetrahydrofuran, 1,4-dioxane, and the like; ketones such as acetone, methyl ethyl ketone, and the like; carboxylic acids such as acetic acid and the like; esters such as ethyl acetate, butyl acetate, and the like; carbonates such as dimethyl carbonate, diethyl carbonate, ethylene carbonate, and the like; alcohols such as methanol, ethanol, propanol, isopropyl alcohol, butanol, and the like; and water. These may be used singly or in combination of two or more kinds.

The amount of the solvent used in the reprecipitation operation varies depending on the kind of polymer and the kind of solvent but, relative to 1 part by mass of the polymer, is usually preferably 0.5 to 100 parts by mass and, more preferably 1 to 50 parts by mass from the viewpoint of economic efficiency.

The weight average molecular weight (Mw) of the polymer is not particularly limited but, if it is 500 to 50,000, more preferably 1,000 to 30,000, and even more preferably 5,000 to 15,000, the polymer is more useful as a component of the photoresist composition mentioned after. Such Mw is a value determined according to the method described in Examples.

Further, the molecular weight distribution (Mw/Mn; Mn represents the number average molecular weight) of the polymer is not particularly limited but is, from the viewpoint of LWR and resolution, preferably 3 or less, more preferably 2.5 or less, and even more preferably 2 or less.

[Photoresist Cmposition]

The photoresist composition of the present invention is prepared by mixing the polymer, a photoacid generator, and a solvent; and, if necessary, a basic compound, a surfactant, and other additives. Hereinafter, each component will be described.

(Photoacid Generator)

The photoacid generator is not particularly limited and heretofore known photoacid generators usually used in a chemically amplified photoresist composition may be used. The photoacid generators include, for example, onium salt-type photoacid generators such as iodonium salts, sulfonium salts, and the like; oxime sulfonate-type photoacid generators; bisalkyl- or bisarylsulfonyl diazomethane-type photoacid generators; nitrobenzylsulfonate-type photoacid generators; iminosulfonate-type photoacid generators; disulfone-type photoacid generators; and the like. These may be used singly or in combination of two or more kinds. Among these, preferable are the onium salt-type photoacid generators and further, from the viewpoint of strength of an acid generated, preferable are the following fluorine-containing onium salts containing fluorine-containing alkyl sulfonate ions as the anion.

Specific examples of the above-mentioned fluorine-containing onium salt include, for example, diphenyliodonium trifluoromethanesulfonate or nonafluorobutanesulfonate; bis (4-tert-butylphenyl)iodonium trifluoromethanesulfonate or nonafluorobutanesulfonate; triphenylsulfonium trifluoromethanesulfonate, heptafluoropropanesulfonate, or nonafluorobutanesulfonate; tri(4-methylphenyl)sulfonium trifluoromethanesulfonate, heptafluoropropanesulfonate, or nonafluorobutanesulfonate; dimethyl(4-hydroxylnaphthyl) sulfonium trifluoromethanesulfonate, heptafluoropropanesulfonate, or nonafluorobutanesulfonate; monophenyldimethylsulfonium trifluoromethanesulfonate, heptafluoropropanesulfonate, or nonafluorobutanesulfonate; diphenylmonomethylsulfonium trifluoromethanesulfonate, heptafluoropropanesulfonate, or nonafluorobutanesulfonate; (4-methylphenyl)diphenylsulfonium trifluoromethanesulfonate, heptafluoropropanesulfonate, or nonafluorobutanesulfonate; (4-methoxyphenyl)diphenylsulfonium trifluoromethanesulfonate, heptafluoropropanesulfonate, or nonafluorobutanesulfonate; tri(4-tert-butyl)phenylsulfonium trifluoromethanesulfonate, heptafluoropropanesulfonate, or nonafluorobutanesulfonate; and the like. These may be used singly or in combination of two or more kinds.

The amount of the photoacid generator blended relative to 100 parts by mass of the polymer is usually preferably 0.1 to 30 parts by mass and more preferably 0.5 to 10 parts by mass from the viewpoint of securing sensitivity and developing characteristics of the photoresist composition.

(Solvent)

The solvent mixed into the photoresist composition includes, for example, glycol ethers such as propylene glycol monoethyl ether, propylene glycol monomethyl ether acetate, ethylene glycol monomethyl ether, ethylene glycol monomethyl ether acetate, ethylene glycol monomethyl ether propionate, ethylene glycol monobutyl ether, ethylene glycol monobutyl ether acetate, diethylene glycol dimethyl ether, and the like; esters such as ethyl lactate, methyl 3-methoxypropionate, methyl acetate, ethyl acetate, propyl acetate, and the like; ketones such as acetone, methyl ethyl ketone, methyl isopropyl ketone, methyl isobutyl ketone, methyl amyl ketone, cyclopentanone, cyclohexanone, and the like; ethers such as diethyl ether, diisopropyl ether, dibutyl ether, tetrahydrofuran, 1,4-dioxane, and the like; and the like. These may be used singly or in a combination of two or more kinds.

The amount of the solvent mixed, relative to 1 part by mass of the polymer, is usually preferably 1 to 50 parts by mass and more preferably 2 to 25 parts by mass.

(Basic Compound)

In order to control the diffusion rate of an acid in a photoresist film and thereby to improve resolution, a basic compound is added optionally, into the photoresist composition in an amount which does not interfere with characteristics thereof. Such a basic compound includes, for example, amides such as formamide, N-methylformamide, N,N-dimethylformamide, acetamide, N-methylacetamide, N,N-dimethylacetamide, N-(1-adamantyl)acetamide, benzamide, N-acetyl ethanolamine, 1-acetyl-3-methylpiperidine, pyrolidone, N-methylpyrrolidone, ε-caprolactam, δ-valerolactam, 2-pyrrolidinone, acrylamide, methacrylamide, t-butylacrylamide, methylenebisacrylamide, methylenebismethacrylamide, N-methylolacrylamide, N-methoxyacrylamide, diacetoneacrylamide, and the like; and amines such as pyridine, 2-methypyridine, 4-methylpyridine, nicotine, quinoline, acridine, imidazole, 4-methylimidazole, benzimidazole, pyrazine, pyrazole, pyrrolidine, N-t-butoxycarbonyl pyrrolidine, piperidine, tetrazole, morpholine, 4-methylmorpholine, piperazine, 1,4-diazabicyclo[2.2.2]octane, tributylamine, tripentylamine, trihexylamine, triheptylamine, trioctylamine, triethanolamine, and the like. These may be used singly or in combination of two or more kinds.

When a basic compound is mixed, the amount thereof blended varies depending on the kind of the basic compound used but, relative to 1 mole of the photoacid generator, is usually preferably 0.01 to 10 moles and more preferably 0.05 to 1 mole.

(Surfactant)

In order to improve coating properties, if desired, a surfactant may further be mixed into the photoresist composition in a range of the amount which does not interfere with the characteristics of the photoresist composition.

Such a surfactant includes, for example, polyoxyethylene lauryl ether, polyoxyethylene stearyl ether, polyoxyethylene oleyl ether, polyoxyethylene n-octylphenyl ether, and the like. These may be used singly or in a combination of two or more kind. When a surfactant is mixed, the amount thereof blended relative to 100 parts by mass of the polymer is usually preferably 2 parts by mass or less.

[Other Additives]

Furthermore, into the photoresist composition, there may be mixed as other additives a sensitizer, an anti-halation agent, a shape-improving agent, a storage stabilizer, an antifoaming agent, and the like in a range of the amount which does not interfere with the characteristics of the photoresist composition.

(Method for Forming Photoresist Pattern)

A predetermined photoresist pattern may be formed by performing a series of operations of coating a photoresist composition on a substrate, prebaking the photoresist film usually preferably at 70 to 160° C. for 1 to 10 minutes, irradiating (exposing) the photoresist film through a predetermined mask, forming a latent pattern by post-exposure baking of the photoresist film preferably at 70 to 160° C. for 1 to 5 minutes, and developing the photoresist film using a developer.

To expose the photoresist film, there may be used radiation of various wavelength ranges, for example, ultraviolet light, X-rays, and the like. For semiconductor photoresist, there are usually used g-line, i-line, and excimer lasers such as XeCl, KrF, KrCl, ArF, ArCl, and the like. Among these, it is preferable to use an ArF excimer laser from the viewpoint of microfabrication.

The exposure amount is preferably 0.1 to 1,000 $mJ/cm^2$ and more preferably 1 to 500 $mJ/cm^2$.

The developer includes basic aqueous solutions wherein there are dissolved inorganic bases such as sodium hydroxide, potassium hydroxide, sodium carbonate, aqueous ammonia, and the like; alkylamines such as ethylamine, diethylamine, triethylamine, and the like; alcohol amines such as dimethylethanolamine, triethanolamine, and the like; quaternary ammonium salts such as tetramethylammonium hydroxide, tetraethylammonium hydroxide, and the like; and the like. Among these, it is preferable to use alkaline aqueous solutions wherein there are dissolved quaternary ammonium salts such as tetramethylammonium hydroxide, tetraethylammonium hydroxide, and the like.

The concentration of the developer is usually preferably 0.1 to 20 mass % and more preferably 0.1 to 10 mass %.

EXAMPLES

Hereinafter, the present invention will be described specifically with reference to Examples and Comparative Examples. However, the present invention is not limited to these Examples. Meanwhile, measurement of purity of the acrylic acid ester derivative (1), measurement of Mw, Mn, and calculation of molecular weight distribution (Mw/Mn) of the polymer were performed according to the following methods.

(Measurement of Purity of the Acrylic Acid Ester Derivative (1))

High-performance liquid chromatography (HPLC) measurement: this was performed by using L-column ODS (manufactured by Chemicals Evaluation and Research Institute, Japan; φ4.6 mm×250 mm) as the column and a UV detector as the detector; and under the conditions including the column temperature of 35° C., the eluent flow rate of 1.0 mL/min, the detector wavelength of 210 nm, and the eluent of a mixed solution of acetonitrile/water (mixing ratio: 50/50 as a volume ratio). The object compound of purity measurement (20 mg) was dissolved in 1.00 g of the above-mentioned eluent and 1.0 μL thereof was injected. After measurement for 50 minutes, the simple area percentage value (%) of the peak obtained was regarded as the purity.

(Measurement of Mw,Mn, and Calculation of Molecular Weight Distribution of the Polymer)

The weight average molecular weight (Mw) and the number average molecular weight (Mn) were measured by gel permeation chromatography (GPC) under the following conditions by using a differential refractometer as a detector and tetrahydrofuran (THF) as an eluent and were obtained as values converted from the calibration curve prepared using standard polystyrene. Further, the molecular weight distribution (Mw/Mn) was determined by dividing the weight average molecular weight (Mw) by the number average molecular weight (Mn).

GPC measurement: this was performed by using two "TSK-gel SUPER HZM-H" (trade name: manufactured by Tosoh Corporation, 4.6 mm×150 mm) and one "TSK-gel SUPER HZ2000" (trade name: manufactured by Tosoh Corporation, 4.6 mm×150 mm) connected in series as the column and under the conditions including the column temperature of 40° C.; the differential refractometer temperature of 40° C.; and the eluent flow rate of 0.35 mL/min.

Example 1

Synthesis of 1-ethylcyclopentan-1-yl (2-methacryloyloxyethyl)carbamate

In a four-necked flask having an inner volume of 500 mL equipped with a thermometer and a stirring apparatus were charged 55.0 g (477 mmol) of 1-ethylcyclopentan-1-ol, 10.0 mg of 4-acetamido-2,2,6,6-tetramethylpiperidine-N-oxyl, 220 g of isopropyl ether, and 75.5 g (477 mmol) of 2-methacryloyloxyethyl isocyanate. After the mixture was cooled by ice water to an inner temperature of 3 to 4° C., 13.8 g (143 mmol) of methanesulfonic acid was added dropwise. After stirring the reaction mixture for 5.5 hours with the reaction temperature maintained at 5 to 6° C., 110.7 g of a saturated aqueous $NaHCO_3$ solution was added dropwise under stirring with the inner temperature maintained at 10° C. or less and, after completion of the dropwise addition, the mixture was allowed to stand still for 30 minutes. After the organic layer (upper layer) formed was separated and washed with 114.7 g of distilled water, 20.7 g of activated carbon was added and the mixture was stirred for 1 hour. The mixture was filtered and to the filtrate obtained was added 1.7 mg of 4-acetoamido-2,2,6,6-tetramethylpiperidine-N-oxyl. The filtrate was concentrated under reduced pressure to obtain 98.9 g of a concentrate (hereinafter referred to as "concentrate A").

In a four-necked flask having an inner volume of 2 L equipped with a thermometer, a stirring apparatus, and a dropping funnel was charged 991 g of hexane and thereto was dropwise added 98.9 g of the concentrate A at an inner temperature range of 21 to 23° C. over a 20-minute period. After completion of the dropwise addition, the mixture was stirred for 1 hour at the same temperature and thereafter filtered through a membrane filter (pore size: 1.0 μm). The filtrate obtained was first warmed to 40° C. and then was cooled to 10° C. at a rate of 15° C./hour. The crystals which precipitated were separated by filtration and the crystals obtained were dried under vacuum (26.7 Pa) at 30° C. for 2 hours to obtain 26.9 g (purity 96.3%, 96.3 mmol, yield: 20.2%) of 1-ethylcyclopentan-1-yl (2-methacryloyloxyethyl)carbamate.

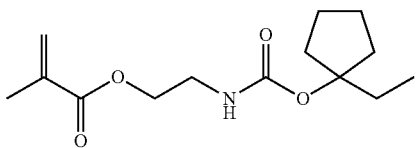 [SMILES: C=C(C)C(=O)OCCNC(=O)OC1(CC)CCCC1]

$^1$H-NMR (400 MHz, CDCl$_3$, TMS, ppm) δ: 6.12 (1H, s), 5.58 (1H, s), 4.80 (1H, br), 4.21 (2H, t, J=5.6 Hz), 3.42-3.48 (2H, m), 2.03-2.15 (2H, m), 1.94-2.03 (5H, m), 1.55-1.75 (6H, m), 0.88 (3H, t, J=7.6 Hz).

Example 2

Synthesis of 4-Methyltetrahydropyran-4-yl (2-methacryloyloxyethyl)carbamate

In a three-necked flask having an inner volume of 50 mL equipped with a thermometer and a stirring apparatus were charged 1.00 g (8.51 mmol) of 4-methyltetrahydropyran-4-ol, 1.0 mg of 4-acetamido-2,2,6,6-tetramethylpiperidine-N-oxyl, 4.0 g of isopropyl ether, and 1.42 g (8.94 mmol) of 2-methacryloyloxyethyl isocyanate. After the mixture was cooled by ice water to an inner temperature of 5° C., 250 mg (2.55 mmol) of methanesulfonic acid was added dropwise. After stirring the reaction mixture for 10 hours with the reaction temperature maintained at 5 to 6° C., 4.0 g of a saturated aqueous NaHCO$_3$ solution was added dropwise with the inner temperature maintained at 10° C. or less and, after completion of the dropwise addition, the mixture was allowed to stand still for 30 minutes. The organic layer (upper layer) formed was separated and the aqueous layer (lower layer) was extracted twice with 4.0 g of isopropyl ether. All the separated organic layers were combined, washed with 4.0 g of distilled water, and the organic layer was concentrated under reduced pressure to obtain 2.29 g of a concentrate. The concentrate was dissolved in 10 g of hexane at 30° C. and the solution was cooled to −10° C. at a rate of 10° C./hour. The crystals which precipitated were separated by filtration and the crystals obtained were dried under vacuum (26.7 Pa) at 30° C. for 2 hours to obtain 1.10 g (purity 97.0%, 3.93 mmol, yield: 46.2%) of 4-methyltetrahydropyran-4-yl (2-methacryloyloxyethyl)carbamate.

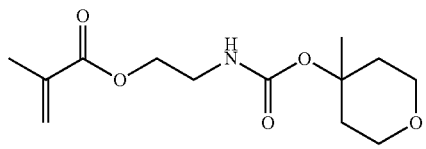 [SMILES: C=C(C)C(=O)OCCNC(=O)OC1(C)CCOCC1]

$^1$H-NMR (400 MHz, CDCl$_3$, TMS, ppm) δ: 6.13 (1H, s), 5.60 (1H, s), 5.00 (1H, br), 4.22 (2H, t, J=5.6 Hz), 3.62-3.72 (4H, m), 3.46 (2H, q, J=5.6 Hz), 2.10-2.14 (2H, m), 1.95 (3H, s), 1.65-1.73 (2H, m), 1.54 (3H, s).

Example 3

Synthesis of 2-methyladamantan-2-yl (2-methacryloyloxyethyl)carbamate

In a three-necked flask having an inner volume of 50 mL equipped with a thermometer and a stirring apparatus were charged 1.66 g (9.98 mmol) of 2-methyl-2-adamantanol, 2.0 mg of 4-acetamido-2,2,6,6-tetramethylpiperidine-N-oxyl, 6.7 g of isopropyl ether, and 1.66 g (10.5 mmol) of 2-methacryloyloxyethyl isocyanate. After the mixture was cooled by ice water to an inner temperature of 5° C., 290 mg (3.0 mmol) of methanesulfonic acid was added dropwise. After stirring the reaction mixture for 15 hours with the reaction temperature maintained at 5 to 6° C., 10 g of a saturated aqueous NaHCO$_3$ solution was added dropwise with the inner temperature maintained at 10° C. or less and, after completion of the dropwise addition, the mixture was allowed to stand still for 30 minutes. The organic layer (upper layer) formed was separated and the aqueous layer (lower layer) was extracted twice with 10 g of isopropyl ether. All the separated organic layers were combined, washed with 10 g of distilled water, and the organic layer concentrated under reduced pressure to obtain 2.82 g of a concentrate. The concentrate was dissolved in 15 g of hexane at 30° C. and the solution was cooled to −10° C. at a rate of 10° C./hour. The crystals which precipitated were separated by filtration and the crystals obtained were dried under vacuum (26.7 Pa) at 30° C. for 2 hours to obtain 1.29 g (purity 98.2%, 3.94 mmol, yield: 39.5%) of 2-methyladamantan-2-yl (2-methacryloyloxyethyl)carbamate.

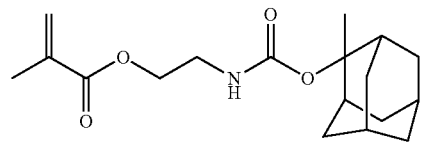 [SMILES: C=C(C)C(=O)OCCNC(=O)OC1(C)C2CC3CC(C2)CC1C3]

$^1$H-NMR (400 MHz, CDCl$_3$, TMS, ppm) δ: 6.13 (1H, s), 5.58 (1H, m), 4.88 (1H, br), 4.22 (2H, t, J=5.6 Hz), 3.46 (2H, dt, J=6.0, 5.6 Hz), 2.26 (2H, br), 1.54-2.05 (18H, m).

Example 4

Synthesis of Polymer (a)

In a three-necked flask having an inner volume of 50 mL equipped with a stirring apparatus, a reflux condenser, and a thermometer were charged 3.42 g (14.6 mmol) of 2-methacryloyloxy-2-methyladamantane, 2.96 g (12.5 mmol) of 3-hydroxyadamantan-1-yl methacrylate, 2.49 g (14.6 mmol) of α-methacryloyloxy-γ-butyrolactone, 0.34 g (1.3 mmol) of 1-ethylcyclopentan-1-yl (2-methacryloyloxyethyl)carbamate synthesized in Example 1, and 36.4 g of methyl ethyl ketone, followed by nitrogen bubbling for 10 minutes. Under a nitrogen atmosphere, 0.36 g (2 mmol) of 2,2'-azobisisobutyronitrile was charged and a polymerization reaction was carried out at 80° C. for 4 hours. The reaction mixture obtained was added dropwise under stirring to 220 g of methanol at room temperature and precipitate which formed was collected by filtration. The precipitate was dried under vacuum (26.7 Pa) at 50° C. for 8 hours to obtain 5.5 g of the polymer (a) containing the following repeating units (the numerical values represent the molar ratio). The weight average molecular weight (Mw) of the polymer (a) obtained was 9,800 and the molecular weight distribution thereof was 1.8.

Polymer (a)

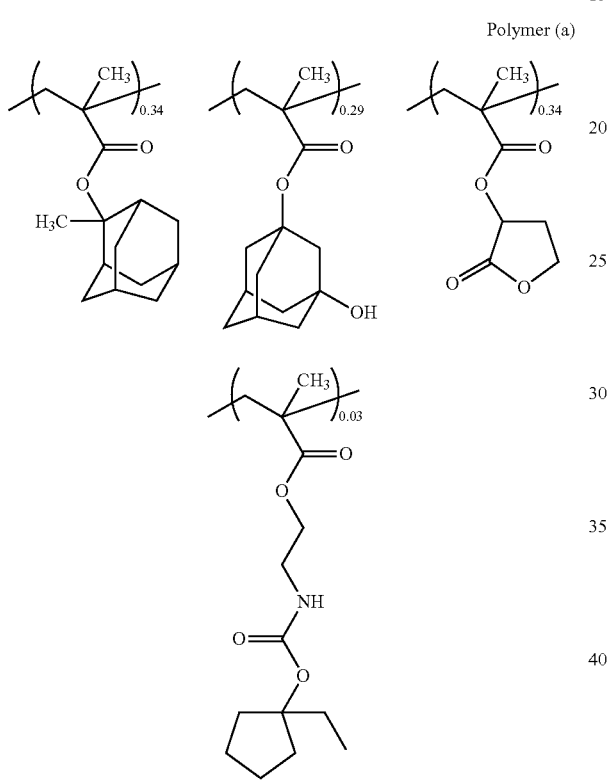

Example 5

Synthesis of Polymer (b)

In a three-necked flask having an inner volume of 50 mL equipped with a stirring apparatus, a reflux condenser, and a thermometer were charged 3.42 g (14.6 mmol) of 2-methacryloyloxy-2-methyladamantane, 2.96 g (12.5 mmol) of 3-hydroxyadamantan-1-yl methacrylate, 2.49 g (14.6 mmol) of α-methacryloyloxy-γ-butyrolactone, 0.34 g (1.3 mmol) of 4-methyltetrahydropyran-4-yl (2-methacryloyloxyethyl)carbamate synthesized in Example 2, and 36.4 g of methyl ethyl ketone, followed by nitrogen bubbling for 10 minutes. Under a nitrogen atmosphere, 0.36 g (2 mmol) of 2,2'-azobisisobutyronitrile was charged and a polymerization reaction was carried out at 80° C. for 4 hours. The reaction mixture obtained was added dropwise under stirring to 220 g of methanol at room temperature and precipitate which formed was collected by filtration. The precipitate was dried under vacuum (26.7 Pa) at 50° C. for 8 hours to obtain 5.0 g of the polymer (b) containing the following repeating units (the numerical values represent the molar ratio). The weight average molecular weight (Mw) of the polymer (b) obtained was 8,900 and the molecular weight distribution thereof was 1.7.

Polymer (b)

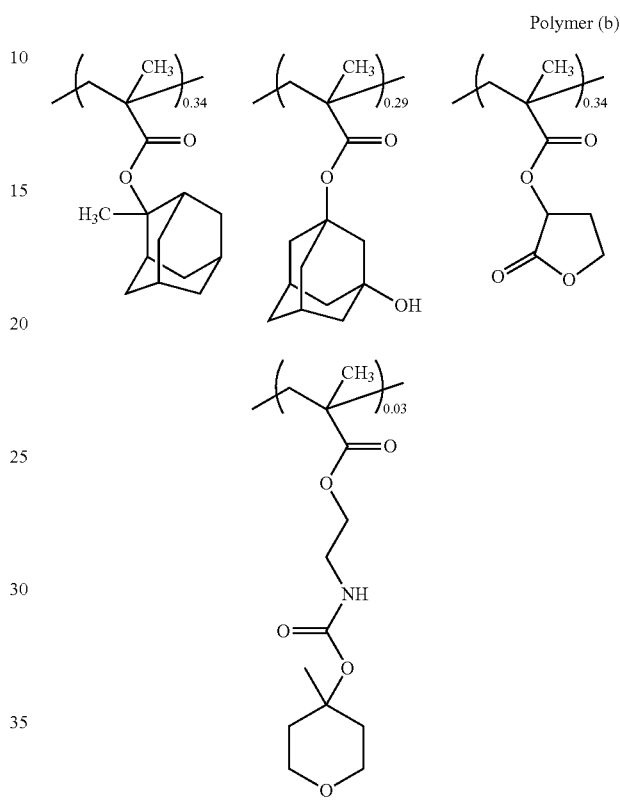

Example 6

Synthesis of Polymer (c)

In a three-necked flask having an inner volume of 50 mL equipped with a stirring apparatus, a reflux condenser, and a thermometer, there were charged 3.42 g (14.6 mmol) of 2-methacryloyloxy-2-methyladamantane, 2.96 g (12.5 mmol) of 3-hydroxyadamantan-1-yl methacrylate, 2.49 g (14.6 mmol) of α-methacryloyloxy-γ-butyrolactone, 0.42 g (1.3 mmol) of 2-methyladamantan-2-yl (2-methacryloyloxyethyl)carbamate synthesized in Example 3 and 36.4 g of methyl ethyl ketone, followed by nitrogen bubbling for 10 minutes. Under a nitrogen atmosphere, 0.36 g (2 mmol) of 2,2'-azobisisobutyronitrile was charged and a polymerization reaction was carried out at 80° C. for 4 hours. The reaction mixture obtained was added dropwise under stirring to 220 g of methanol at room temperature and precipitate which formed was collected by filtration. The precipitate was dried under vacuum (26.7 Pa) at 50° C. for 8 hours to obtain 4.9 g of the polymer (c) containing the following repeating units (the numerical values represent the molar ratio). The weight average molecular weight (Mw) of the polymer (c) obtained was 9,800 and the molecular weight distribution thereof was 1.7.

Polymer (c)

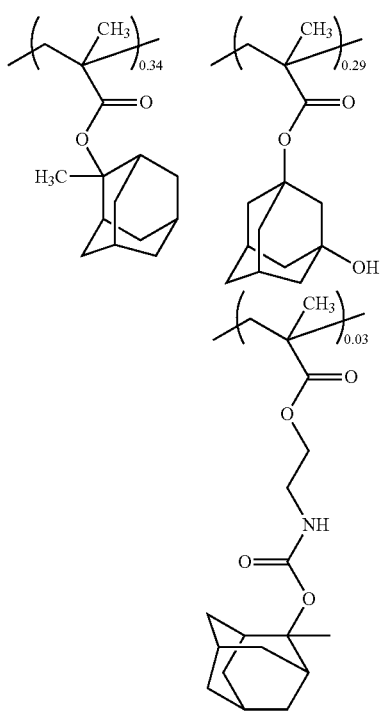

Comparative Synthetic Example 1

Synthesis of Polymer (d)

In a three-necked flask having an inner volume of 50 mL equipped with a stirring apparatus, a reflux condenser, and a thermometer were charged 3.42 g (14.6 mmol) of 2-methacryloyloxy-2-methyladamantane, 2.96 g (12.5 mmol) of 3-hydroxyadamantan-1-yl methacrylate, 2.49 g (14.6 mmol) of α-methacryloyloxy-1-γ-butyrolactone, and 36.4 g of methyl ethyl ketone, followed by nitrogen bubbling for 10 minutes. Under a nitrogen atmosphere, 0.36 g (2 mmol) of 2,2'-azobisisobutyronitrile was charged and a polymerization reaction was carried out at 80° C. for 4 hours. The reaction mixture obtained was added dropwise under stirring to 220 g of methanol at room temperature and precipitate which formed was collected by filtration. The precipitate was dried under vacuum (26.7 Pa) at 50° C. for 8 hours to obtain 5.6 g of the polymer (d) containing the following repeating units (the numerical values represent the molar ratio). The weight average molecular weight (Mw) of the polymer (d) obtained was 10,200 and the molecular weight distribution thereof was 1.8.

Polymer (d)

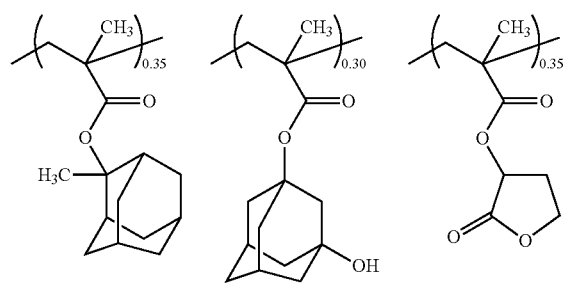

Comparative Synthetic Example 2

Synthesis of Polymer (e)

In a three-necked flask having an inner volume of 50 mL equipped with a stirring apparatus, a reflux condenser, and a thermometer were charged 3.42 g (14.6 mmol) of 2-methacryloyloxy-2-methyladamantane, 2.96 g (12.5 mmol) of 3-hydroxyadamantan-1-yl methacrylate, 2.49 g (14.6 mmol) of α-methacryloyloxy-γ-butyrolactone, 0.34 g (1.3 mmol) of t-butyl-4-(methacryloyloxy)piperidine-1-carboxylate, and 36.4 g of methyl ethyl ketone, followed by nitrogen bubbling for 10 minutes. Under a nitrogen atmosphere, 0.36 g (2 mmol) of 2,2'-azobisisobutyronitrile was charged and a polymerization reaction was carried out at 80° C. for 4 hours. The reaction mixture obtained was added dropwise under stirring to 220 g of methanol at room temperature and precipitate which formed was collected by filtration. The precipitate was dried under vacuum (26.7 Pa) at 50° C. for 8 hours to obtain 5.0 g of the polymer (e) containing the following repeating units (the numerical values represent the molar ratio). The weight average molecular weight (Mw) of the polymer (e) obtained was 10,400 and the molecular weight distribution thereof was 1.6.

Polymer (e)

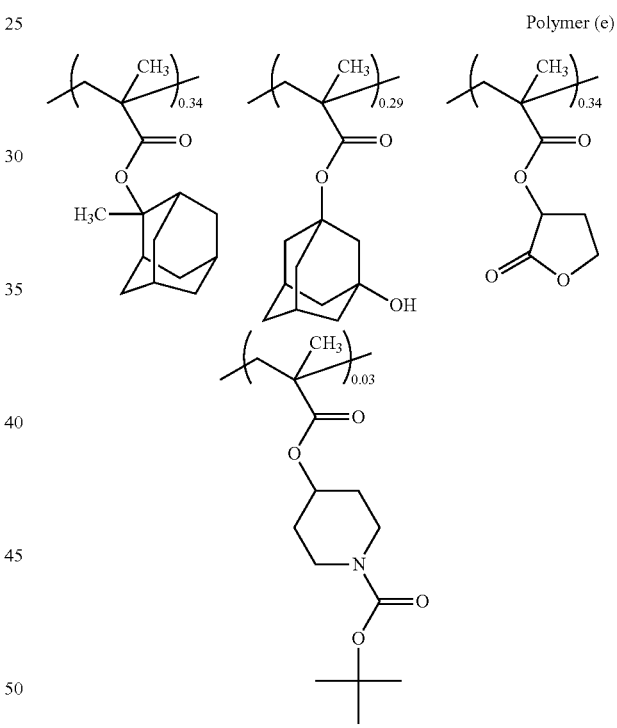

Examples 7, 8, and 9 and Comparative Examples 1 and 2

Five kinds of photoresist compositions were prepared by mixing 100 parts by mass of each of the polymers obtained in Examples 4, 5, and 6 and in Comparative Examples 1 and 2 [five kinds, namely (a), (b), (c), (d), and (e)], 4.5 parts by mass of "TPS-109" (trade name, component: triphenylsulfonium nonafluoro-n-butanesulfonate, produced by Midori Kagaku Co., Ltd.) as a photoacid generator, and 1896 parts by mass of a mixed solvent of propylene glycol monomethyl ether acetate and cyclohexanone (mass ratio=1:1) as a solvent.

These photoresist compositions were filtered using a membrane filter having a pore size of 0.2 μm. First, a 100 nm-thick antireflective coating (base coating) was prepared by coating a 10 cm-diameter silicon wafer with a 6 mass % solution of cresol-novolac resin ("PS-6937" produced by Gun Ei Chemical Industry Co., Ltd.) in propylene glycol monomethyl ether acetate by a spin-coating method, followed by baking the wafer on a hot plate at 200° C. for 90 seconds. Then, a 300 nm-thick photoresist film was prepared by coating the silicon wafer with each of the filtrates by a spin-coating method, followed by prebaking the wafer on a hot plate at 130° C. for 90 seconds. This photoresist film was subjected to exposure by a two-beam interference method using an ArF excimer laser at a wavelength of 193 nm. Subsequently, this was subjected to post-exposure bake at 130° C. for 90 seconds and thereafter a 1:1 line and space pattern was formed by developing with a 2.38 mass % aqueous tetramethylammonium hydroxide solution for 60 seconds. The developed wafer was cleaved and a piece was observed by a scanning electron microscope (SEM) to examine the pattern shape of and to measure the variation in line width roughness (LWR) of the exposed line and space pattern resolved at 1:1 and having a line width of 100 nm.

LWR was evaluated with dispersion (3σ) of line width variation as an index, wherein the line width was measured at plural points on the observing monitor. Furthermore, the cross-sectional shape of the pattern was examined using a scanning electron microscope (SEM) and was evaluated based on the following criteria:

good: the pattern has high rectangularity (being close to a rectangle); and poor: T-tops or microbridges are formed with low rectangularity.

The results are shown in Table 1 and Table 2.

Comparative Example 3

Photoresist processing and evaluation were conducted in the same manner as in Comparative Example 1, except that, in Comparative Example 1, a photoresist composition was prepared by mixing 100 parts by mass of the polymer (d), 4.5 parts by mass of "TPS-109" (trade name, component: triphenylsulfonium nonafluoro-n-butanesulfonate, produced by Midori Kagaku Co., Ltd.) as a photoacid generator, 3.0 parts by mass of N-t-butoxycarbonyldi-n-octylamine as an acid diffusion controlling agent, and 1896 parts by mass of a mixture of propylene glycol monomethyl ether acetate and cyclohexanone (mass ratio=1:1) as a solvent. The results are shown in Table 2.

TABLE 1

| | Polymer used | LWR (nm) | Pattern shape |
|---|---|---|---|
| Example 7 | 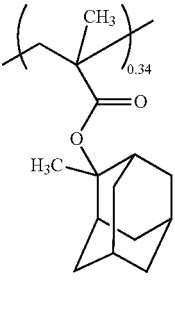 Polymer (a) | 8.0 | Good |
| Example 8 | 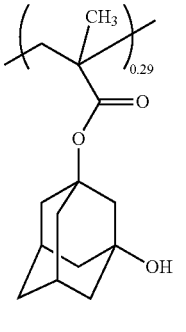 Polymer (b) | 8.3 | Good |

TABLE 1-continued
| | Polymer used | LWR (nm) | Pattern shape |
|---|---|---|---|
| Example 9 | 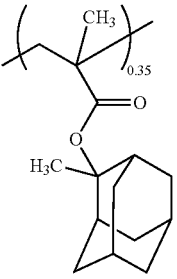 Polymer (c) | 8.9 | Good |
TABLE 2
| | Polymer and additive used | LWR (nm) | Pattern shape |
|---|---|---|---|
| Comparative example 1 | 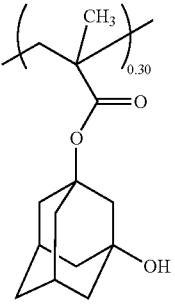 Polymer (d) | 11.4 | Poor |
| Comparative example 2 | 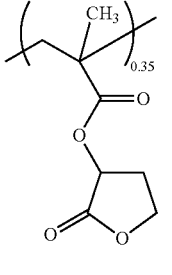 Polymer (e) | 9.2 | Good |

TABLE 2-continued

| | Polymer and additive .used | LWR (nm) | Pattern shape |
|---|---|---|---|
| Comparative example 3 | 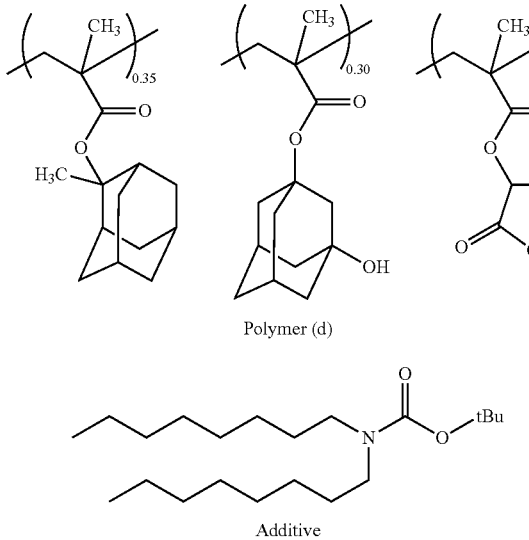<br>Polymer (d)<br><br>Additive | 9.4 | Good |

From the above, a photoresist composition containing a polymer (polymers (a), (b), and (c)) containing a structural unit derived from the acrylic acid ester derivative (1) of the present invention has been shown to form a photoresist pattern with a good shape and improved LWR, compared to a photoresist composition containing a polymer (polymers (d) and (e)) obtained by polymerization without using the acrylic acid ester derivative (1) of the present invention or a photoresist composition obtained by combining a polymer (polymer (d)) obtained by polymerization without using the acrylic acid ester derivative (1) and an acid diffusion controlling agent. That is, both formation of a high resolution photoresist pattern and reduction of LWR are satisfied at the same time.

INDUSTRIAL APPLICABILITY

The acrylic ester derivative of the present invention is useful as a raw material of a polymer for a photoresist composition which can form a photoresist pattern with improved LWR and a good shape.

The invention claimed is:

1. An acrylic acid ester derivative represented by the following general formula (1):

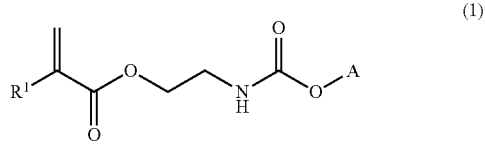 (1)

wherein $R^1$ is a hydrogen atom or a methyl group; and A represents the following general formula (A-1) or (A-2):

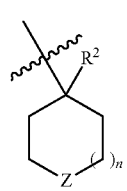 (A-1)

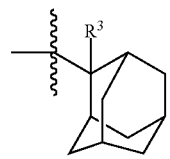 (A-2)

wherein $R^2$ and $R^3$ are each independently an alkyl group having 1 to 6 carbon atoms or a cyclic hydrocarbon group having 3 to 6 carbon atoms; Z is $CH_2$ or —O—; and n is 0 or 1; with the proviso that in (A-1) there is no case where $R^2$ is a methyl group and Z is $CH_2$ and n is 1.

2. A polymer comprising a structural unit derived from the acrylic acid ester derivative according to claim 1.

3. A photoresist composition comprising the polymer according to claim 2, a photoacid generator, and a solvent.

4. The acrylic acid ester derivative according to claim 1, wherein A represents the general formula (A-1).

5. The acrylic acid ester derivative according to claim 1, wherein A represents the general formula (A-2).

6. The acrylic acid ester derivative according to claim 1, wherein said acrylic acid ester derivative is one of the following compounds:

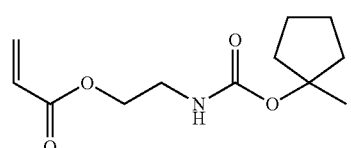

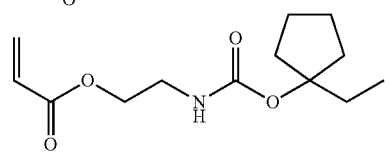

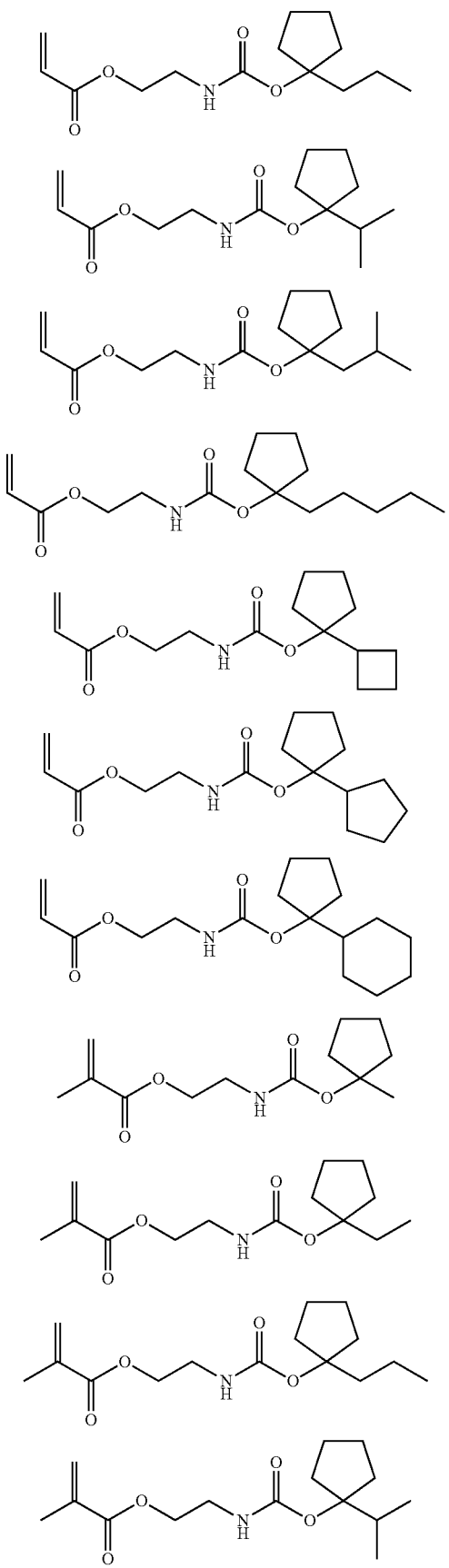
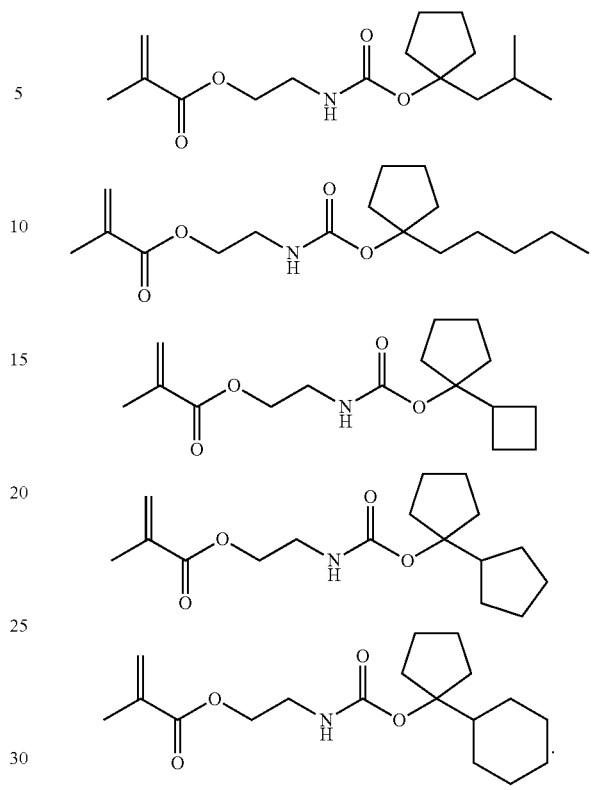
7. The acrylic acid ester derivative according to claim 1, wherein said acrylic acid ester derivative is one of the following compounds:
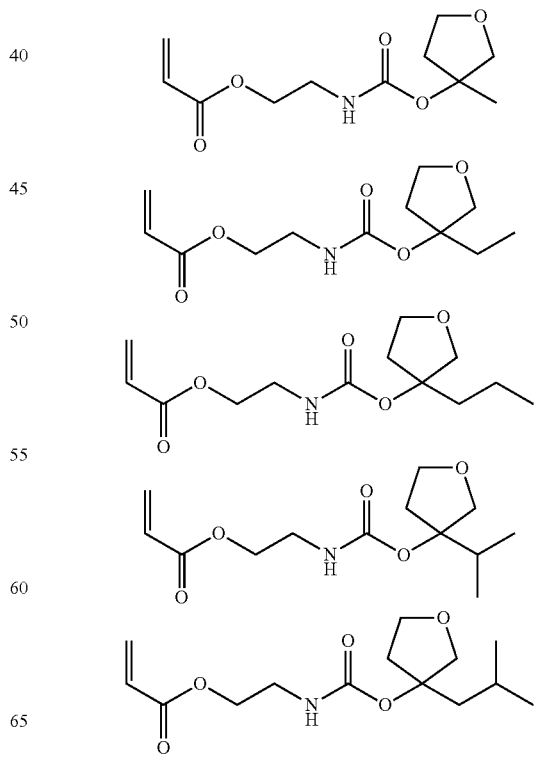

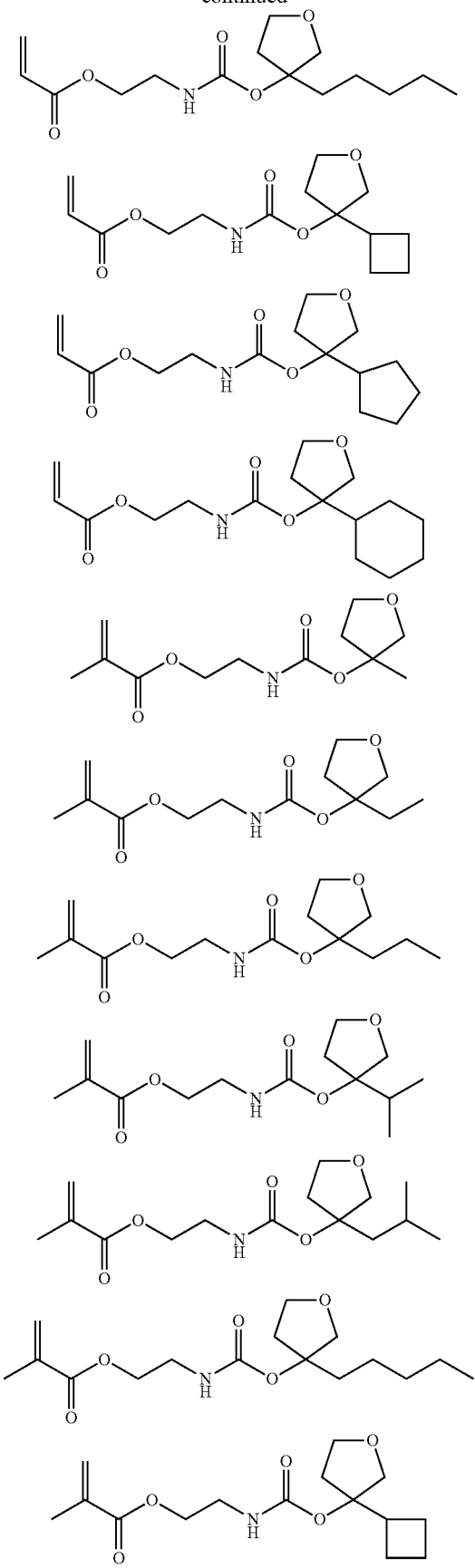
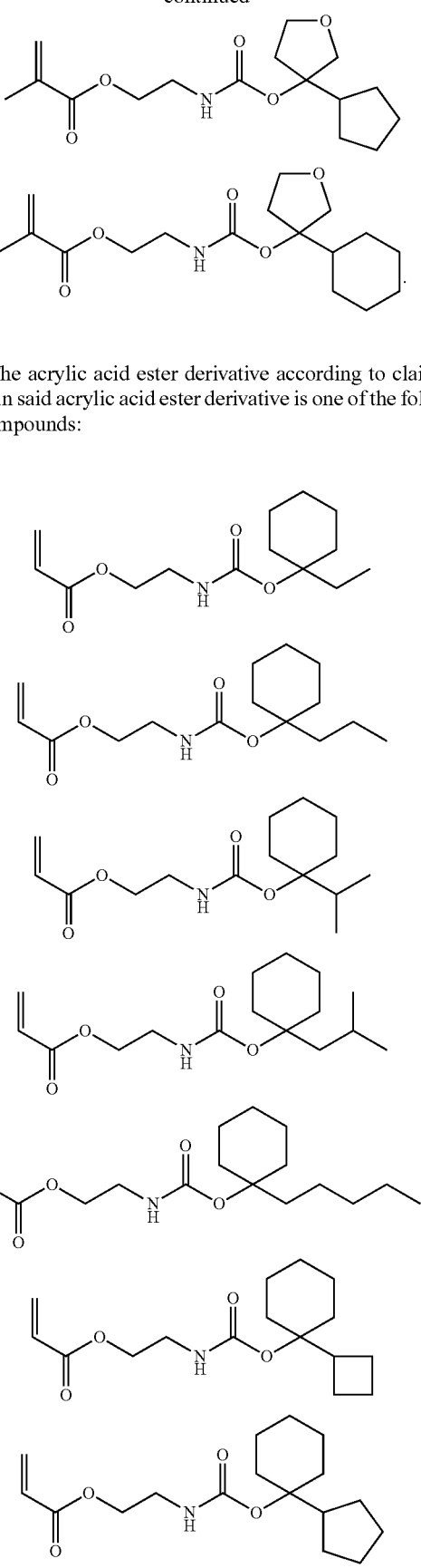
8. The acrylic acid ester derivative according to claim 1, wherein said acrylic acid ester derivative is one of the following compounds:

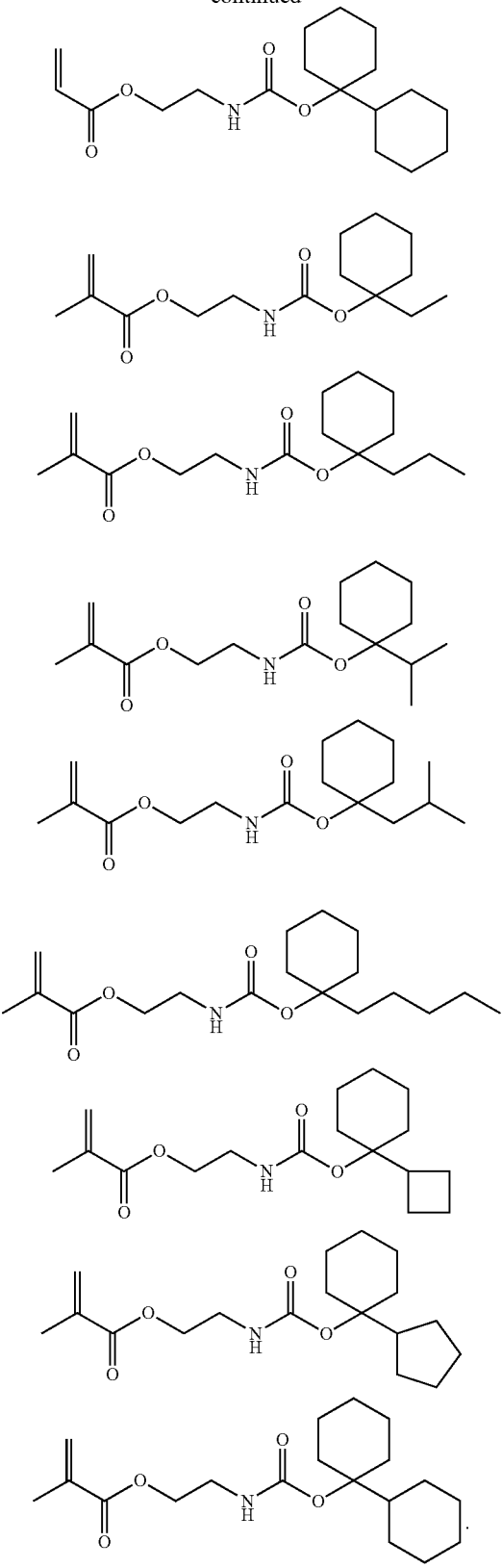
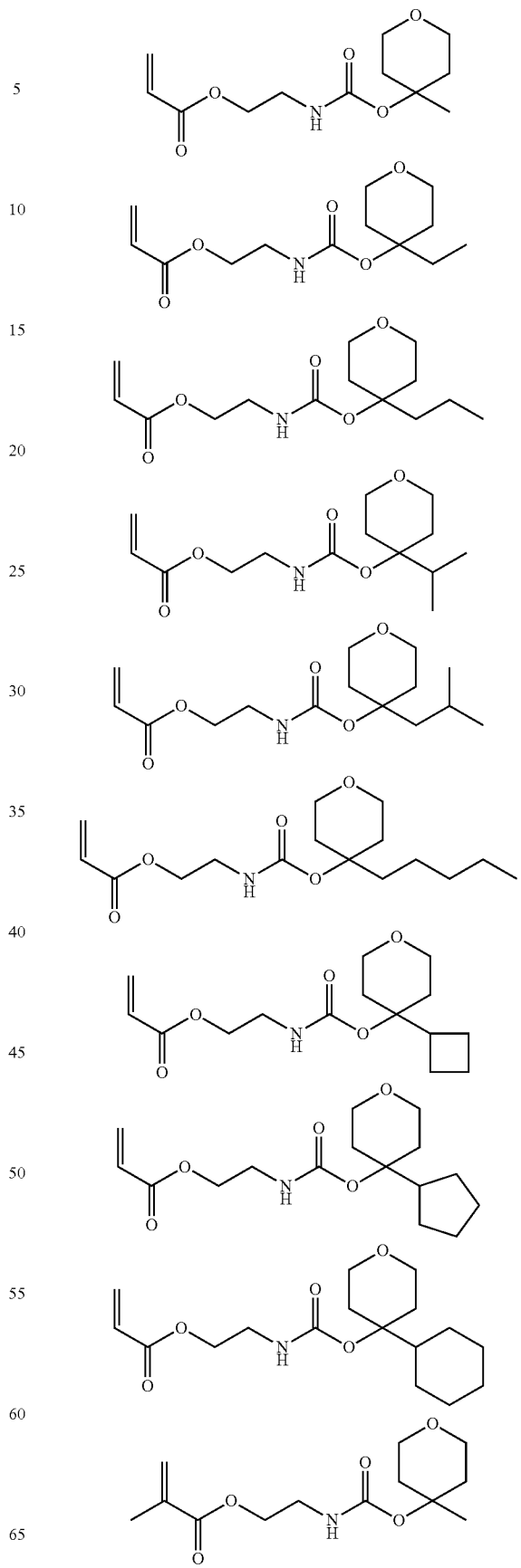
9. The acrylic acid ester derivative according to claim 1, wherein said acrylic acid ester derivative is one of the following compounds:

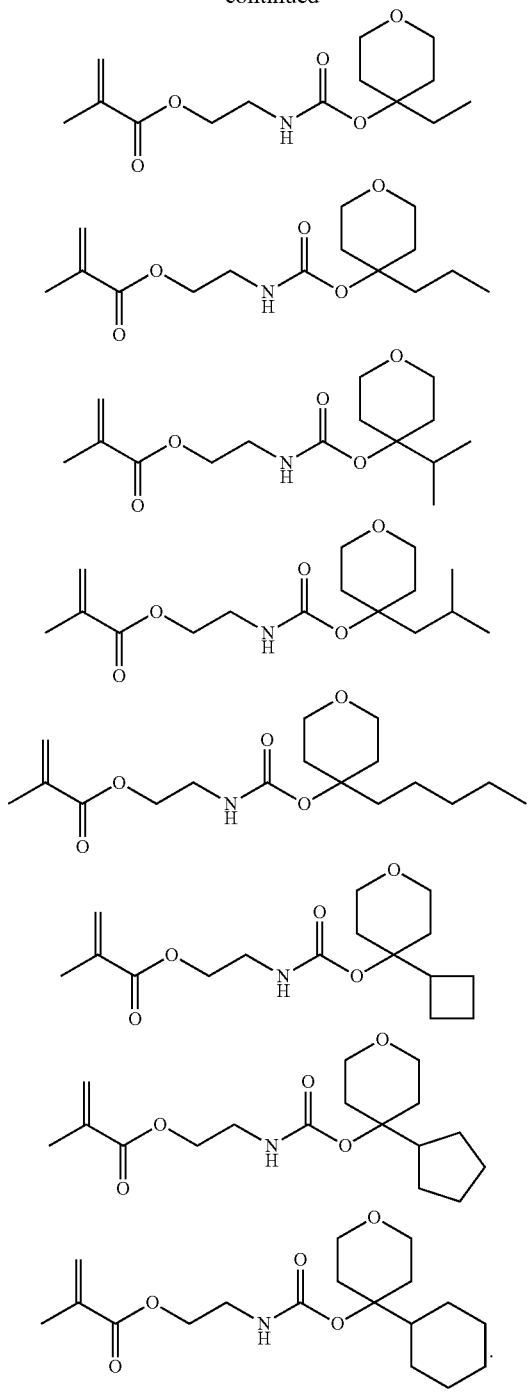
10. The acrylic acid ester derivative according to claim 1, wherein said acrylic acid ester derivative is one of the following compounds:
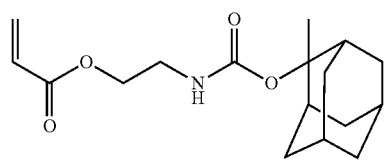
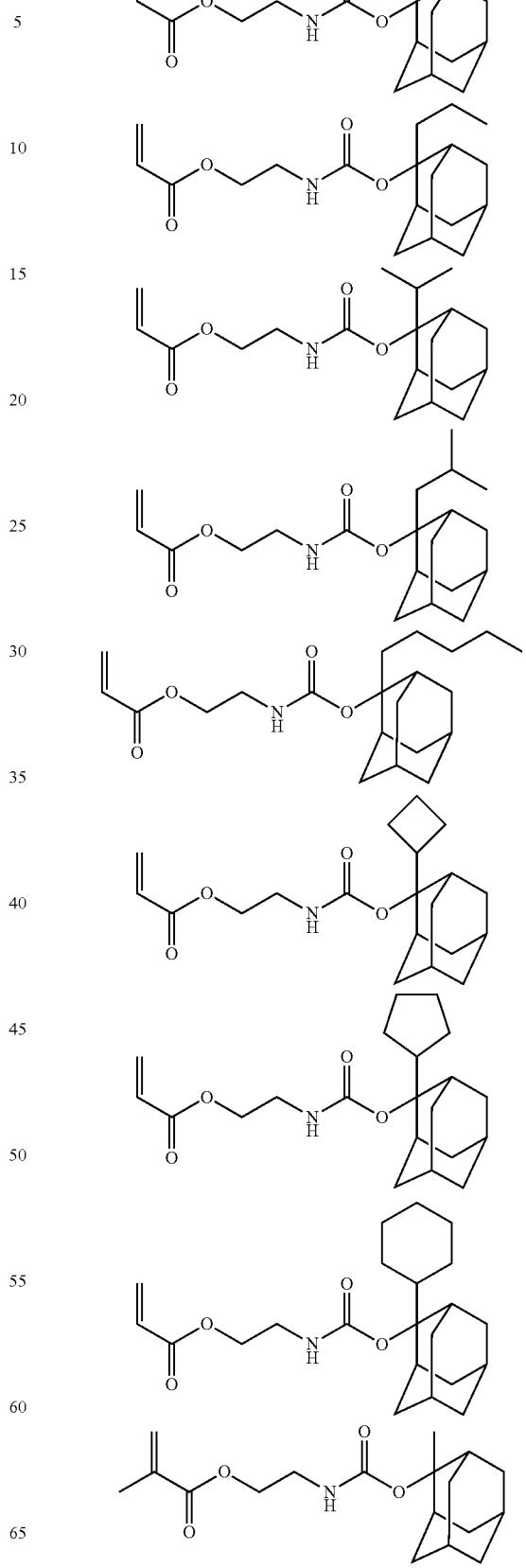

-continued

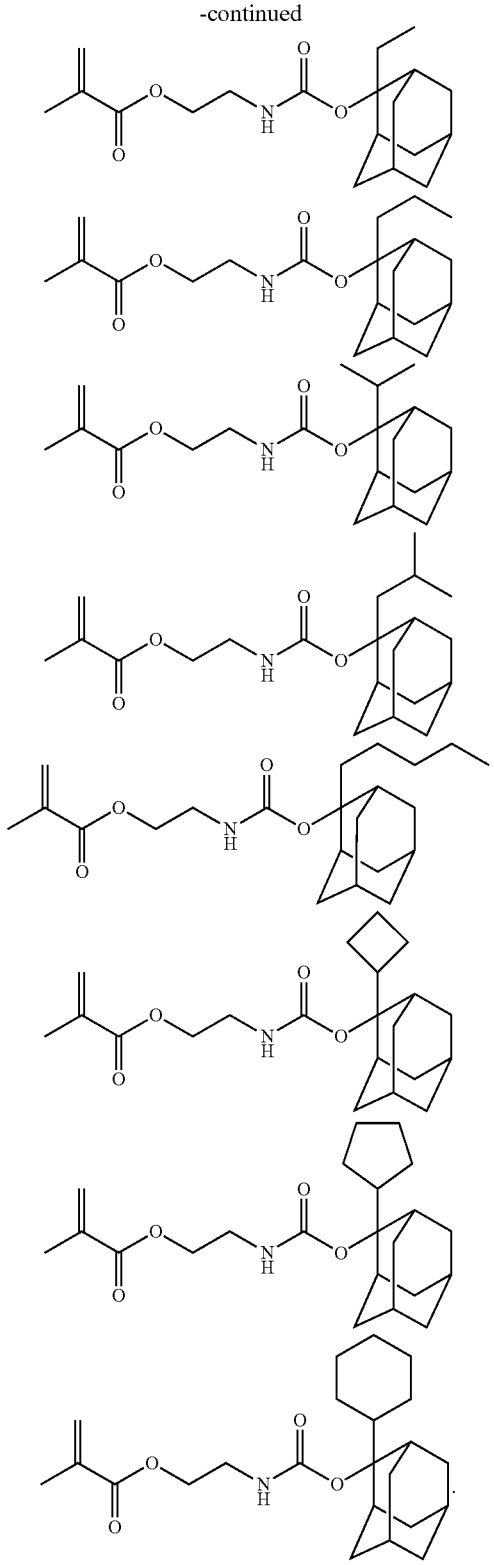

11. A polymer comprising a structural unit derived from the acrylic acid ester derivative according to claim 4.

12. A polymer comprising a structural unit derived from the acrylic acid ester derivative according to claim 5.

13. A polymer comprising a structural unit derived from the acrylic acid ester derivative according to claim 6.

14. A polymer comprising a structural unit derived from the acrylic acid ester derivative according to claim 7.

15. A polymer comprising a structural unit derived from the acrylic acid ester derivative according to claim 8.

16. A polymer comprising a structural unit derived from the acrylic acid ester derivative according to claim 9.

17. A polymer comprising a structural unit derived from the acrylic acid ester derivative according to claim 10.

18. The polymer according to claim 11, further comprising a structural unit derived from at least one of the following compounds:

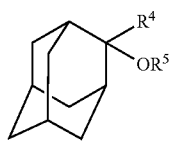 (I)

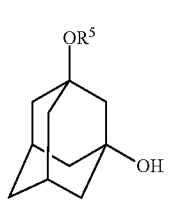 (II)

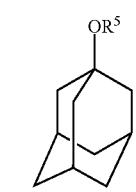 (III)

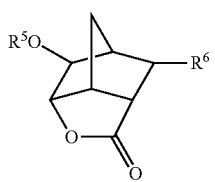 (IV)

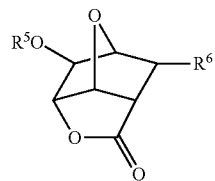 (V)

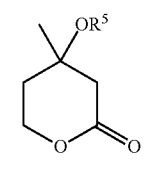 (VI)

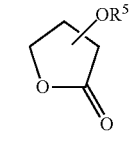 (VII)

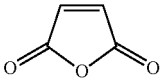 (VIII)

(IX)

$R^5-O-R^8$ (X)

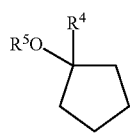
(XI)

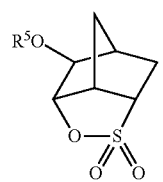
(XII)

where $R^4$ represents a hydrogen atom or an alkyl group having 1 to 3 carbon atoms; $R^5$ represents a polymerizable group; $R^6$ represents a hydrogen atom or —COOR$^7$; $R^7$ represents an alkyl group having 1 to 3 carbon atoms; and $R^8$ represents an alkyl group having from 1 to 4 carbon atoms.

19. The polymer according to claim 12, further comprising a structural unit derived from at least one of the following compounds:

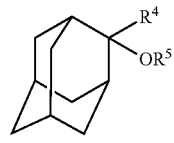
(I)

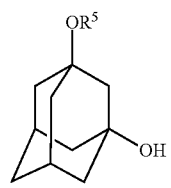
(II)

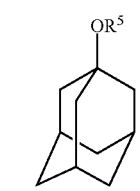
(III)

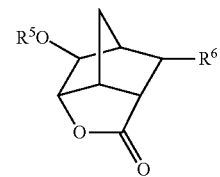
(IV)

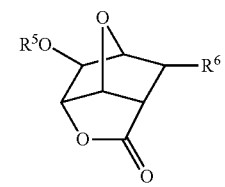
(V)

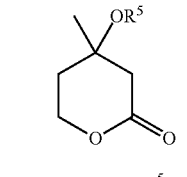
(VI)

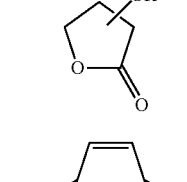
(VII)

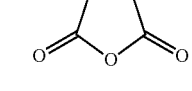
(VIII)

(IX)

$R^5-O-R^8$ (X)

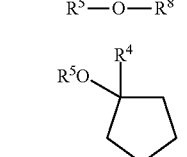
(XI)

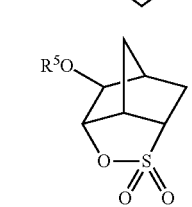
(XII)

where $R^4$ represents a hydrogen atom or an alkyl group having 1 to 3 carbon atoms; $R^5$ represents a polymerizable group; $R^6$ represents a hydrogen atom or —COOR$^7$; $R^7$ represents an alkyl group having 1 to 3 carbon atoms; and $R^8$ represents an alkyl group having from 1 to 4 carbon atoms.

* * * * *